(12) United States Patent
Dubaquie et al.

(10) Patent No.: US 6,509,443 B1
(45) Date of Patent: Jan. 21, 2003

(54) IGF-I POINT VARIANTS

(75) Inventors: Yves Dubaquie, San Francisco, CA (US); Henry Lowman, El Granada, CA (US)

(73) Assignee: Genentech, Inc., South San Francisco, CA (US)

( * ) Notice: Subject to any disclaimer, the term of this patent is extended or adjusted under 35 U.S.C. 154(b) by 39 days.

(21) Appl. No.: 09/723,896

(22) Filed: Nov. 28, 2000

Related U.S. Application Data

(62) Division of application No. 09/477,923, filed on Jan. 5, 2000.
(60) Provisional application No. 60/115,010, filed on Jan. 6, 1999.

(51) Int. Cl.[7] .......................... C07K 14/65; C07K 1/00; A61K 38/30; A61K 38/28

(52) U.S. Cl. ...................... 530/303; 530/350; 530/399; 514/3

(58) Field of Search ............................. 514/3; 530/303, 530/350, 399

(56) References Cited

U.S. PATENT DOCUMENTS

| | | | |
|---|---|---|---|
| 5,077,276 A | 12/1991 | Ballard et al. | 514/12 |
| 5,164,370 A | 11/1992 | Ballard et al. | 514/12 |
| 5,342,763 A | 8/1994 | Swartz | 435/69.1 |
| 5,470,828 A | 11/1995 | Ballard et al. | 514/12 |
| 5,514,646 A | 5/1996 | Chance et al. | 514/3 |
| 5,714,460 A | 2/1998 | Gluckman et al. | 514/3 |
| 5,750,373 A | 5/1998 | Garrard et al. | 435/69.4 |
| 5,821,047 A | 10/1998 | Garrard et al. | 435/5 |
| 5,834,250 A | 11/1998 | Wells et al. | 435/7.1 |
| 5,891,722 A | 4/1999 | Fuks et al. | 435/346 |

FOREIGN PATENT DOCUMENTS

| | | |
|---|---|---|
| EP | 128733 | 12/1984 |
| EP | 214826 | 3/1987 |
| EP | 230869 | 8/1987 |
| EP | 288451 | 10/1988 |
| EP | 294021 | 12/1988 |
| EP | 369943 | 5/1990 |
| EP | 375438 | 6/1990 |
| EP | 742228 | 11/1996 |
| EP | 965596 | 12/1999 |
| WO | WO 89/05822 | 6/1989 |
| WO | WO 89/08667 | 9/1989 |
| WO | WO 89/09268 | 10/1989 |
| WO | WO 89/09792 | 10/1989 |
| WO | WO 94/04569 | 3/1994 |
| WO | WO 96/33216 | 10/1996 |
| WO | WO 97/39032 | 10/1997 |
| WO | WO 98/45427 | 10/1998 |
| WO | WO 98/56406 | 12/1998 |
| WO | WO 99/32620 | 7/1999 |
| WO | WO 00/23469 | 4/2000 |
| WO | WO 00/69901 | 11/2000 |

OTHER PUBLICATIONS

Bowie et al. Deciphering the Message in Protein Sequences:Tolerance to Amino Acid Substitutions. *Science* 247:1306–1310 (1990).*

Wells, JA Additivity of Mutational Effects in Proteins. *Biochemistry* 29:8509–8517 (1990).*

Bach and Rechler, "Insulin–like Growth Factor Binding Proteins" *Diabetes Reviews* 3:38–61 (1995).

Bagley et al., "A key functional role for the insulin–like growth factor 1 N–terminal pentapeptide" *Biochemical Journal* 259(3):665–671 (May 1, 1989).

Bar et al., "Tissue localization of perfused endothelial cell IGF binding protein is markedly altered by association with IGF–I" *Endocrinology* 127(6):3234–3245 (1990).

Barnett and Owens, "Insulin analogues" *Lancet* 349(9044):47–51 (Jan. 4, 1997).

Bass et al., "Hormone Phage: An Enrichment Method for Variant Proteins with Altered Binding Properties" *Proteins: Structure, Function, and Genetics* 8(4):309–314 (1990).

Baxter & Martin, "Binding Proteins for Insulin–Like Growth Factors in Adult Rat Serum. Comparison With Other Human and Rat Binding Proteins" *Biochem. & Biophys. Res. Comm.* 147(1):408–415 (1987).

Baxter et al., "Recommendations for nomenclature of the insulin–like growth factor binding protein superfamily" *Endocrinology* 139(10):4036 (Oct. 1998).

Baxter et al., "Structural determinants for binary and ternary complex formation between insulin–like growth factor–I (IGF–I) and IGF binding protein–3" *Journal of Biological Chemistry* 267(1):60–65 (Jan. 5, 1992).

Baxter, R., "The Insulin–Like Growth Factors and Their Binding Proteins" *Comp. Biochem. Physiol.* 91B(2):229–235 (1988).

Bayne et al., "Structural analogs of human insulin–like growth factor I with reduced affinity for serum binding proteins and the type 2 insulin–like growth factor receptor" *Journal of Biological Chemistry* 263:6233–6239 (1988).

Bayne et al., "The C region of human insulin–like growth factor (IGF) I is required for high affinity binding to the type 1 IGF receptor" *Journal of Biological Chemistry* 264(19):11004–11008 (Jul. 5, 1989).

Bayne et al., "The roles of tyrosines 24, 31, and 60 in the high affinity binding of insulin–like growth factor–I to the type I insulin–like growth factor receptor" *Journal of Biological Chemistry*.

(List continued on next page.)

*Primary Examiner*—Elizabeth Kemmerer
*Assistant Examiner*—Regina M. DeBerry
(74) *Attorney, Agent, or Firm*—Janet E. Hasak

(57) ABSTRACT

IGF-I and insulin variants are provided that selectively bind to IGFBP-1 or IGFBP-3. These agonist variants are useful, for example, to improve the half-lives of IGF-I and insulin, respectively.

3 Claims, 8 Drawing Sheets

OTHER PUBLICATIONS

Binkert et al., "Cloning, sequence analysis and expression of a cDNA encoding a novel insulin–like growth factor binding protein (IGFBP–2)" *EMBO Journal* 8:2497–2502 (1989).

Bogan and Thorn, "Anatomy of hot spots in protein interfaces" *Journal of Molecular Biology* 280(1):1–9 (Jul. 3, 1998).

Bornfeldt et al., "Binding and biological effects of insulin, insulin analogues and insulin–like growth factors in rat aortic smooth muscle cells. Comparison of maximal growth promoting activities" *Diabetologia* 34(5):307–313 (May 1991).

Brange et al., "Designing insulin for diabetes therapy by protein engineering" *Current Opinion in Structural Biology* 1:934–940 (1991).

Brange et al., "Monomeric insulins obtained by protein engineering and their medical implications" *Nature* 333(6174):679–682 (Jun. 16, 1988).

Brange, J., "Insulin Preparations" *Galenics of Insulin, The Physico–chemical and Pharmaceutical Aspects of Insulin and Insulin Preparations*, New York:Springer–Verlag pp. 17–40 (1987).

Brems et al., "Altering the association properties of insulin by amino acid replacement" *Protein Engineering* 5(6):527–533 (1992).

Brewer et al., "Cloning, Characterization, and Expression of a Human Insulin–Like Growth Factor Binding Protein" *Biochem. & Biophys. Res. Comm.* 152(3):1289–1297 (1988).

Brinkman et al., "Isolation and characterization of a cDNA encoding the low molecular weight insulin–like growth factor binding protein (IBP–1)" *The EMBO J.* 7:2417–2423 (1988).

Cara et al., "An insulin–like growth factor I/insulin hybrid exhibiting high potency for interaction with the type I insulin–like growth factor and insulin receptors of placental plasma membranes" *Journal of Biological Chemistry* 265(29):17820–17825 (Oct. 15, 1990).

Cascieri et al., "Mutants of human insulin–like growth factor I with reduced affinity for the type 1 insulin–like growth factor receptor" *Biochemistry* 27(9):3229–3233 (May 3, 1988).

Cascieri et al., "Structural analogs of human insulin–like growth factor (IGF) I with altered affinity for type 2 IGF receptors" *Journal of Biological Chemistry* 264:2199–2202 (1989).

Chang et al., "Single–Step Solubilization and Folding of IGF–1 Aggregates from *Escherichia coli*" *Protein Folding: In Vivo and In Vitro*, American Chemical Society, Chapter 14, pp. 178–188 (1993).

Chernausek et al., "Proteolytic cleavage of insulin–like growth factor binding protein 4 (IGFBP–4). Localization of cleavage site to non–homologous region of native IGFVP–4" *Journal of Biological Chemistry* 270(19):11377–11382 (May 12, 1995).

Clackson et al., "A Hot Spot of Binding Energy in a Hormone–Receptor Interface" *Science* 267:383–386 (1995).

Clark and Robinson, "Up and down the growth hormone cascade" *Cytokine & Growth Factor Reviews* 7(1):65–80 (Jun. 1996).

Clemmons et al., "Competition for binding to insulin–like growth factor (IGF) binding protein–2, 3, 4, and 5 by the IGFs and IGF analogs" *Endocrinology* 131(2):890–895 (Aug. 1992).

Clemmons et al., "Discrete Alterations of the Insulin–like Growth Factor I Molecule Which Alter Its Affinity for Insulin–like Growth Factor–binding Proteins Result in Changes in Bioactivity" *Journal of Biological Chemistry* 265(21):12210–12216 (1990).

Clemmons, D., "Insulin–like growth factor binding proteins and their role in controlling IGF actions" *Cytokine & Growth Factor Reviews* 8(1):45–62 (Mar. 1997).

Conover, "Potentiation of insulin–like growth factor (IGF) action by IGF–binding protein–3: studies of underlying mechanism" *Endocrinology* 130(6):3193–3199 (Apr. 1992).

Conover, C., "Insulin–like growth factor binding protein proteolysis in bone cell models" *Progress in Growth Factor Research* 6(2–4):301–309 (1995).

Cooke et al., "Solution Structures of Human Insulin–Like Growth Factor 1: A Nuclear Magnetic Resonance and Restrained Molecular Dynamics Study " *Biochemistry* 30:5484–5491 (1991).

Cunningham et al., "High–Resolution Epitope Mapping of hGH–Receptor Interactions by Alanine–Scannine Mutagenesis " *Science* 244:1081–1085 (Jun. 1989).

Cunningham et al., "Production of an Atrial Natriuretic Peptide Variant that is Specific for Type A Receptor" *EMBO Journal* 13(11):2508–2515 (1994).

DeWolf et al., "Solution structure of a mini IGF–1" *Protein Science* 5(11):2193–2202 (Nov. 1996).

Di Cera, E., "Site–specific thermodynamics: understanding cooperativity in molecular recognition" *Chem. Rev.* 98:1563–1591 (1998).

DiMarchi et al., "Synthesis of a fast–acting insulin analog based on structural homology with insulin–like growth factor–I" *Peptides: Chemistry and Biology* (Proceedings of the Twelfth American Peptide Symposium), J.A. Smith and J.E. Rivier, eds., Leiden:ESCOM pp. 26–28 (1992).

Dodd et al., "Reversible adsorption of soluble hexamieric insulin onto the surface of insulin crystals cocrystallized with protamine: an electrostatic interaction" *Pharmaceutical Research* 12(1):60–68 (Jan. 1995).

Drejer, K., "The bioactivity of insulin analogues from in vitro receptor binding to in vivo glucose uptake" *Diabetes–Metabolism Reviews* 8(3):259–285 (Oct. 1992).

Dubaquie et al., "Total Alanine–Scanning Mutagenesis of Insulin–Like Growth Factor I (IGF–I) Identifies Differential Binding Epitopes for IGFBP–1 and IGFBP–3" *Biochemistry* 38(20):6386–6396 (1999).

Garrett et al., "Crystal structure of the first three domains of the type–1 insulin–like growth factor receptor" *Nature* 394(6691):395–399 (Jul. 12, 1998).

Heding et al., "Biosensor measurement of the binding of insulin–like growth factors I and II and their analogues to the insulin–like growth factor–binding protein–3" *Journal of Biological Chemistry* 271(24):13948–13952 (Jun. 14, 1996).

Hober et al., "Disulfide Exchange Folding of Insulin–Like Growth Factor I" *Biochemistry* 31:1749–1756 (1992).

Howey et al., "[Lys(B28), Pro (B29)]–Human Insulin: an Equipotent Analog of Human Insulin with Rapid Onset and Short Duration of Action" *Diabetes* (Abstract #1688) 40(Suppl 1):423A (1991).

Hua et al., "Native and non–native structure in a protein–folding intermediate: spectroscopic studies of partially reduced IGF–I and an engineered alanine model" *Journal of Molecular Biology* 259(2):297–313 (Jun. 7, 1996).

Jansson et al., "Structural Changes in Insulin–Like Growth Factor (IGF) I Mutant Proteins Affecting Binding Kinetic Rates to IGF Binding Protein 1 and IGF–I Receptor" *Biochemistry* 36:4108–4117 (1997).

Jansson et al., "The Insulin–like Growth Factor (IGF) Binding Protein 1 Binding Epitope on IFG–I Probed by Heteronuclear NMR Spectroscopy and Mutational Analysis" *The Journal of Biololgical Chemistry* 273(38):24701–24707 (Sep. 18, 1998).

Joly et al., "Overexpression of *Escherichia coli* oxidoreductases increases recombinant insulin–like growth factor–I accumulation" *Proc. Natl. Acad. Sci. USA* 95:2773–2777 (Mar. 1998).

Jones et al., "Insulin–Like Growth Factors and Their Binding Proteins: Biological Actions" *Endocrine Reviews* 16(1):3–34 (1995).

Kalus et al., "Structure of the IGF–binding domain of the insulin–like growth factor–binding protein–5 (IGFBP–5): implications for IGF and IGF–I receptor interactions" *EMBO Journal* 17(22):6558–6572 (Nov. 16, 1998).

Kang et al., "Comparison of subcutaneous soluble human insulin and insulin analogues ($Asp^{B9}$, $Glu^{B27}$; $Asp^{B10}$; $Asp^{B28}$) on meal–related plasma glucose excursions in type I diabetic subjects" *Diabetes Care* 14(7)–571–577 (Jul. 1991).

Kelley et al., "Analysis of the Factor VIIa Binding Site on Human Tissue Factor: Effects of Tissue Factor Mutations on the Kinetics and Thermodynamics of Binding" *Biochemistry* 34(33):10383–10392 (1995).

King et al., "Production and characterization of recombinant insulin–like growth factor–I (IGF–I) and potent analogues of IGF–I, with Gly or Arg substituted for $Glu^3$, following their expression in *Escherichia coli* as fusion proteins" *Journal of Molecular Endocrinology* 8(1):29–41 (Feb. 1992).

Kunkel et al., "Efficient site–directed mutagenesis using uracil–containing DNA" *Methods in Enzymology* 204:125–139 (1991).

Lassalle et al., "ESM–1 is a novel human endothelial cell–specific molecule expresed in lung and regulated by cytokines" *Journal of Biological Chemistry* 271:20458–20464 (1996).

Lee et al., "Insulin–Like Growth Factor (IGF) Binding Complementary Deoxyribonucleic Acid from Human HEP G2 Hepatoma Cells: Predicted Protein Sequence Suggests an IGF Binding Domain Different from Those of the IGF–I and IGF–II Receptors" *Mol. Endocrinol.* 2(5):404–411 (1988).

Leung et al., "Growth hormone receptor and serum binding protein: purification, cloning and expression" *Nature* 330:537–543 (1987).

Loddick et al., "Displacement of insulin–like growth factors from their binding proteins as a potential treatment for stroke" *Proc. Natl. Acad. Sci. USA* 95(4):1894–1898 (Feb. 17, 1998).

Lowman and Wells, "Affinity maturation of human growth hormone by monovalent phage display" *Journal of Molecular Biology* 234(3):564–578 (1993).

Lowman et al., "Molecular mimics of insulin–like growth factor 1 (IGF–1) for inhibiting IGF–1: IGF–binding protein interactions" *Biochemistry* 37(25):8870–8878 (1998).

Lowman et al., "Selecting High–Affinity Binding Proteins by Monovalent Phage Display" *Biochemistry* 30(45):10832–10838 (1991).

Lowman, H., "Phage display of peptide libraries on protein scaffolds" *Methods in Molecular Biology*, Chapter 24, 87:249–264 (1998).

Magee et al., "Insulin–like growth factor I and its binding proteins: a study of the binding interface using B–domain analogues" *Biochemistry* 38(48):15863–15870 (Nov. 30, 1999).

Manes et al., "Functional epitope mapping of insulin–like growth factor I (IGF–I) by Anti–IGF–I monoclonal antibodies" *Endocrinology* 138(3):905–915 (1997).

Martin & Baxter, "Insulin–like Growth Factor–binding Protein from Human Plasma. Purification and Characterization" *Journal of Biological Chemistry* 261(19):8754–8760 (1986).

Martin & Baxter, "Regulation and actions of the insulin–like growth factor binding proteins" *Current Opinion in Endocrinology and Diabetes* pp. 16–21 (1994).

McInnes and Sykes, "Growth factor receptors: structure, mechanism, and drug discovery" *Biopolymers* 43(5):339–366 (1997).

Miller et al., "Oxidative refolding of insulin–like growth factor 1 yields two products of similar thermodynamic stability: a bifurcating protein–folding pathway" *Biochemistry* 32:5203–5213 (1993).

Oh et al., "Characterization of the affinities of insulin–like growth factor (IGF)–binding proteins 1–4 for IGF–I, IGF–II, IGF–I/insulin hybrid, and IGF–I analogs" *Endocrinology* 132:1337–1344 (1993).

Oh et al., "Synthesis and characterization of insulin–like growth factor–binding protein (IGFBP)–7. Recombinant human mac25 protein specifically binds IGF–I and –II" *Journal of Biological Chemistry* 271:30322–30325 (1996).

Peterkofsky et al., "Elevated Activity of Low Molecular Weight Insulin–Like Growth Factor–Binding Proteins in Sera of Vitamin C–Deficient and Fasted Guinea Pigs" *Endocrinology* 128(4):1769–1779 (1991).

Simpson et al., "Insulin–like growth factor–I and diabetes. A review" *Growth Hormone and IGF Research* 8:83–95 (1998).

Slieker and Sundell, "Modifications in the 28–29 position of the insulin B–chain alter binding to the IGF–I receptor with minimal effect on insulin receptor binding" *Diabetes* (Abstract #670) 40(Suppl. 1):168A (1991).

Slieker et al., "Insulin and IGF–I Analogs: Novel Approaches to Improved Insulin Pharmacokinetics" *Adv. Experimental Med. Biol.* 343:25–32 (1994).

Swisshelm et al., "Enhanced expression of an insulin growth factor–like binding protein (mac25) in senescent human mammary epithelial cells and induced expression with retinoic acid" *Proc. Natl. Acad. Sci.* 92:4472–4476 (1995).

Terasawa et al., "Solution structure of human insulin–like growth factor II; recognition sites for receptors and binding proteins" *EMBO Journal* 13(23):5590–5597 (Dec. 1, 1994).

Torres et al., "Solution structure of human insulin–like growth factor II. Relationship to receptor and binding protein interactions" *Journal of Molecular Biology* 248(2):385–401 (Apr. 28, 1995).

Ullrich et al., "Insulin–like growth factor I receptor primary structure: comparison with insulin receptor suggests structural determinants that define functional specificity" *EMBO Journal* 5(10):2503–2512 (1986).

Weiss et al., "Heteronuclear 2D NMR studies of an engineered insulin monomer: assignment and characterization of the receptor–binding surface by selective $^2$H and $^{13}$C labeling with application to protein design" *Biochemistry* 30(30):7373–7389 (Jul. 30, 1991).

Wolpert et al., "Identification of an insulin analog with enhanced growth effect in aortic smooth muscle cells" *Diabetes* 39(Suppl. 1):140A (1990).

Wood et al., "Cloning and expression of the growth hormone–dependent insulin–like growth factor–binding protein" *Molecular Endocrinology* 2:1176–1185 (1988).

Yamauchi et al., "Purification and molecular cloning of prostacylin–stimulating factor from serum–free conditioned medium of human diploid fibroblast cells" *Biochemical Journal* 303(Part 2):591–598 (1994).

* cited by examiner

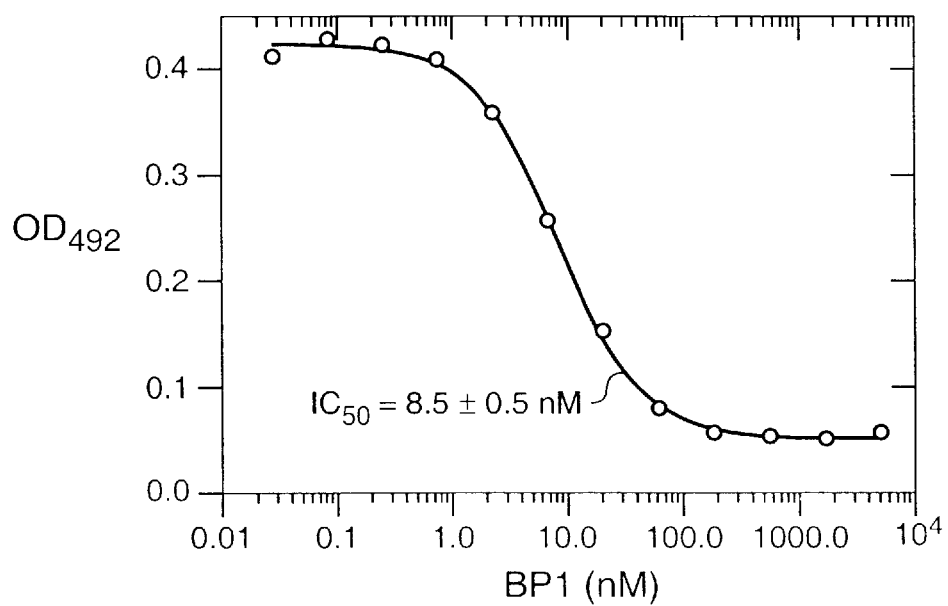
FIG._1A
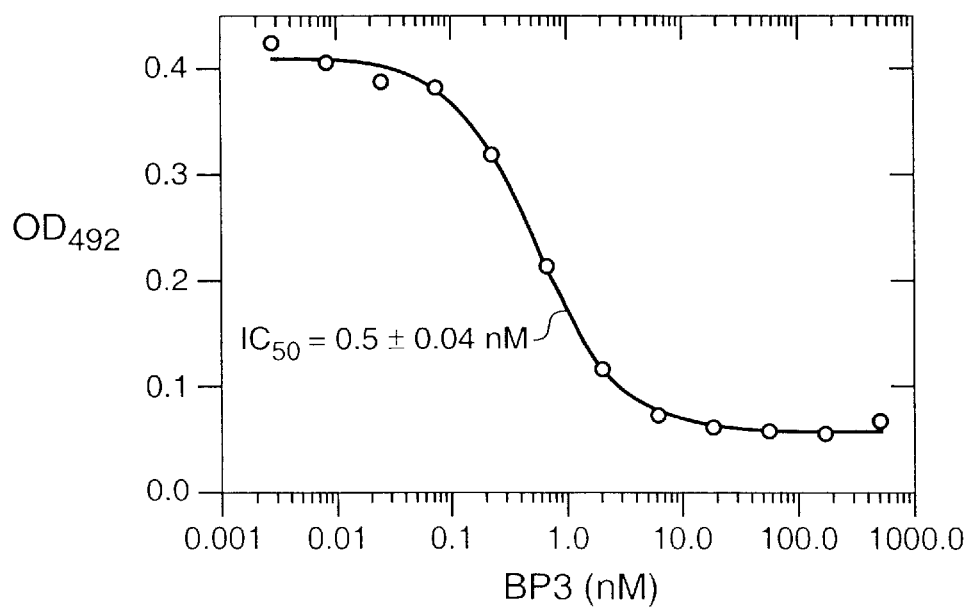
FIG._1B

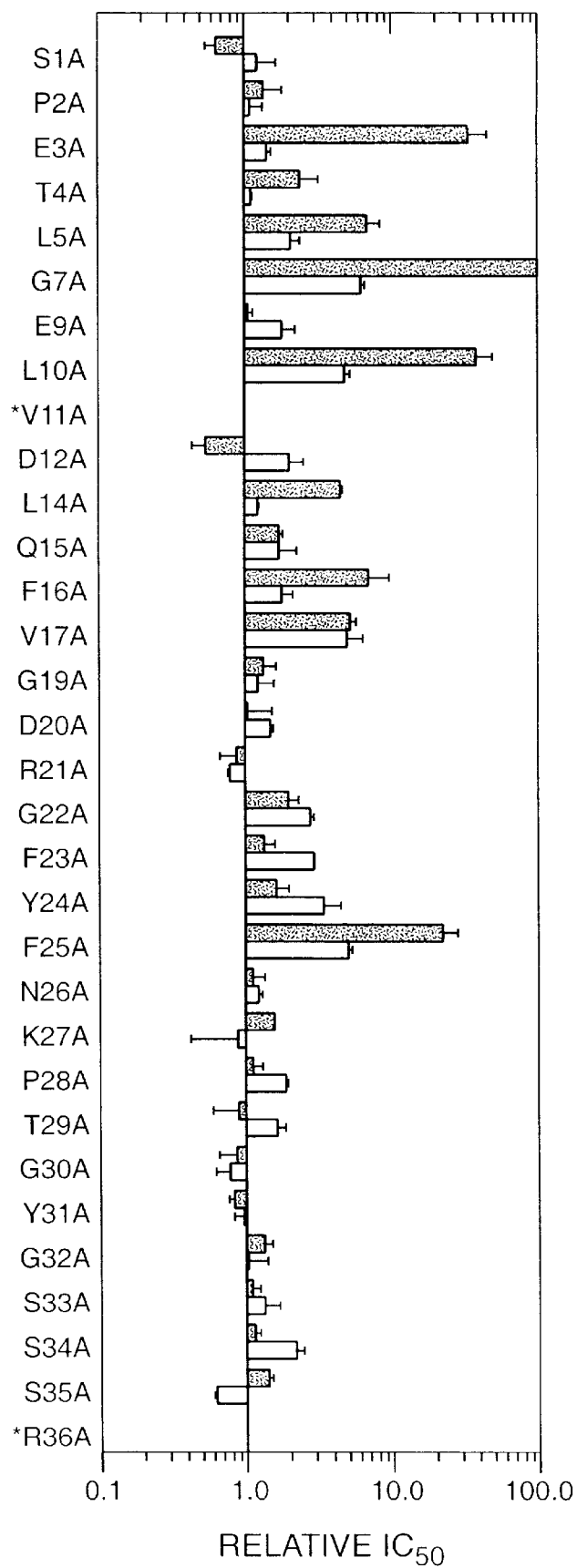
FIG._2A

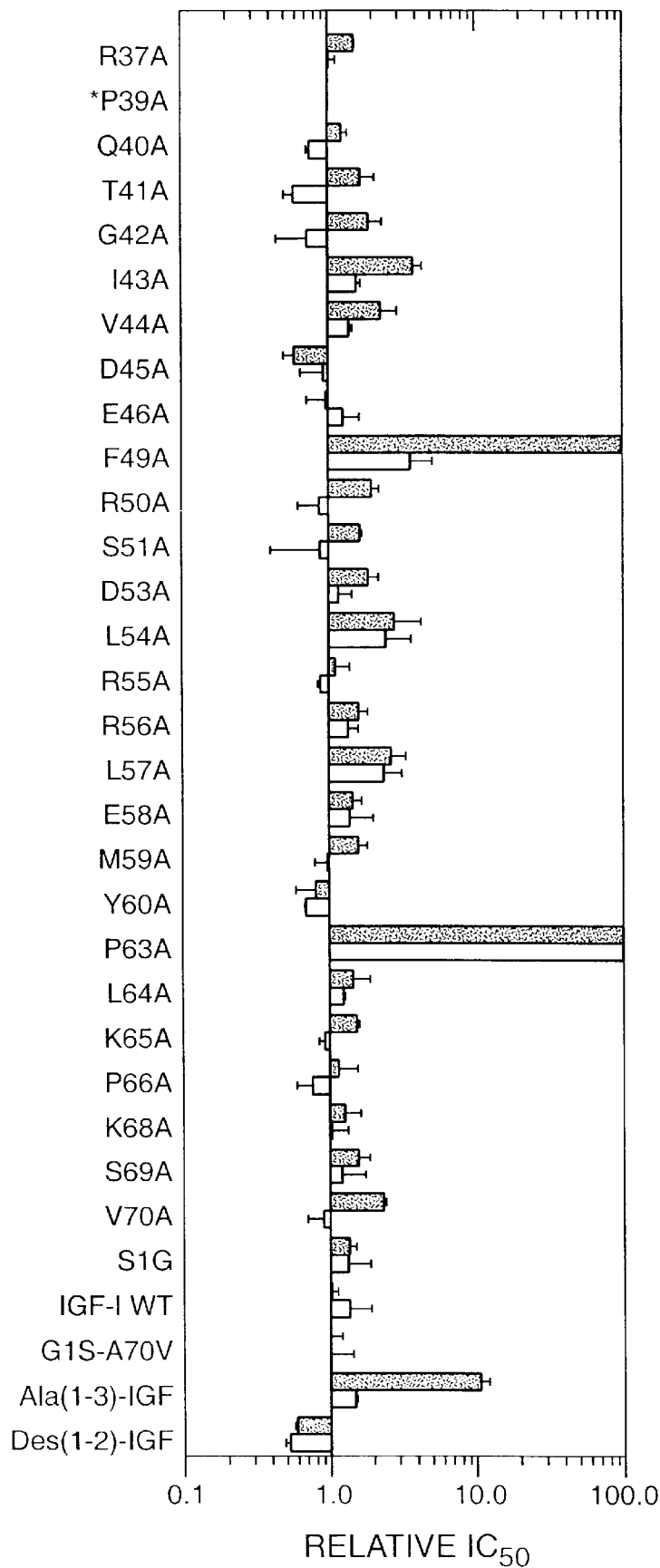
FIG._2B

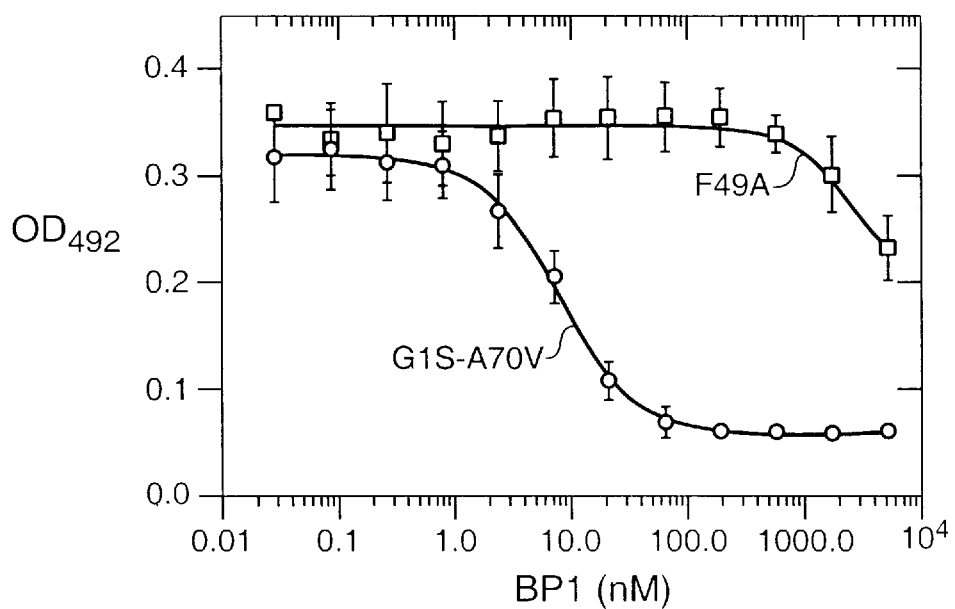
FIG._3A
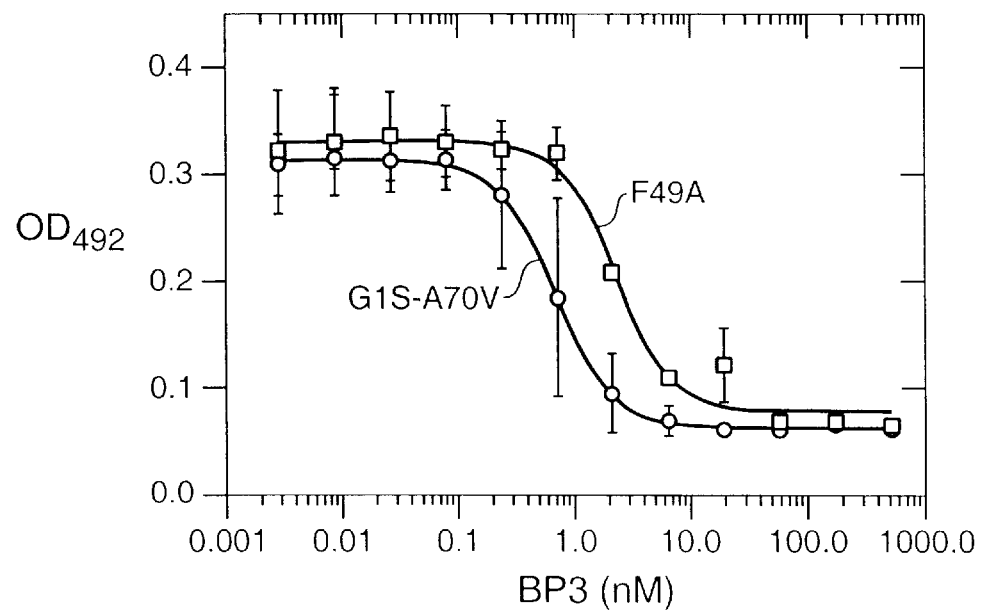
FIG._3B

```
              10        20                        30
wtIGF    GPETLCGAELVDALQFVCGDRGFYFNKPT---------------GYGS
          . ***..**.** .***.***..   *              * *.
proin-   FVNQHLCGSHLVEALYLVCGERGFFYTPKTRREAEDLQVGQVELGGGPGA
sulin          10        20        30        40         50

. ***..**.** .***.***..   *
insulin  FVNQHLCGSHLVEALYLVCGERGFFYTPKT
(B chain)      10        20        30

40        50        60        70
wtIGF    SSRRA-------PQTGIVDECCFRSCDLRRLEMYCAPLKPAKSA
          .*  ..        . ***..**    * * .** **
proin-   GSLQPLALEGSLQKRGIVEQCCTSICSLYQLENYCN
sulin              60        70        80
                          ***..**    * * .** **
insulin                  GIVEQCCTSICSLYQLENYCN
(A chain)                  31        40        50
```

FIG._4

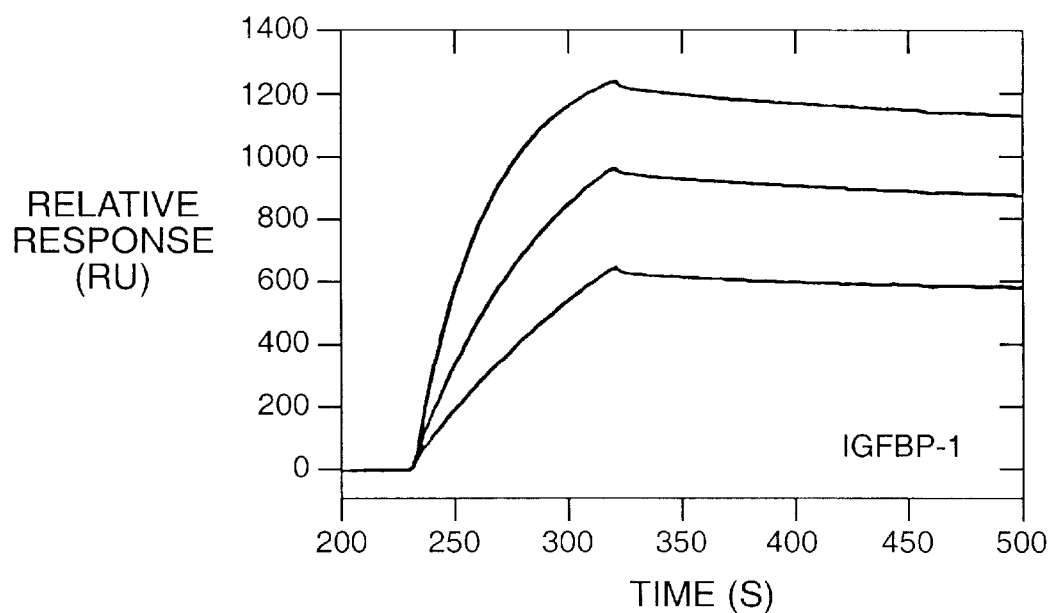
FIG._5A
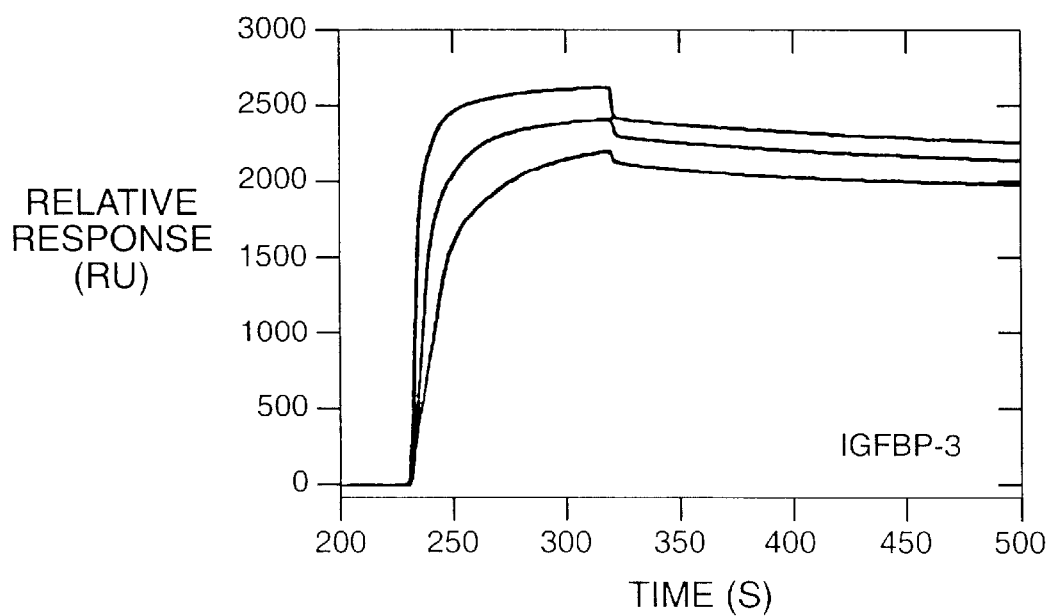
FIG._5B

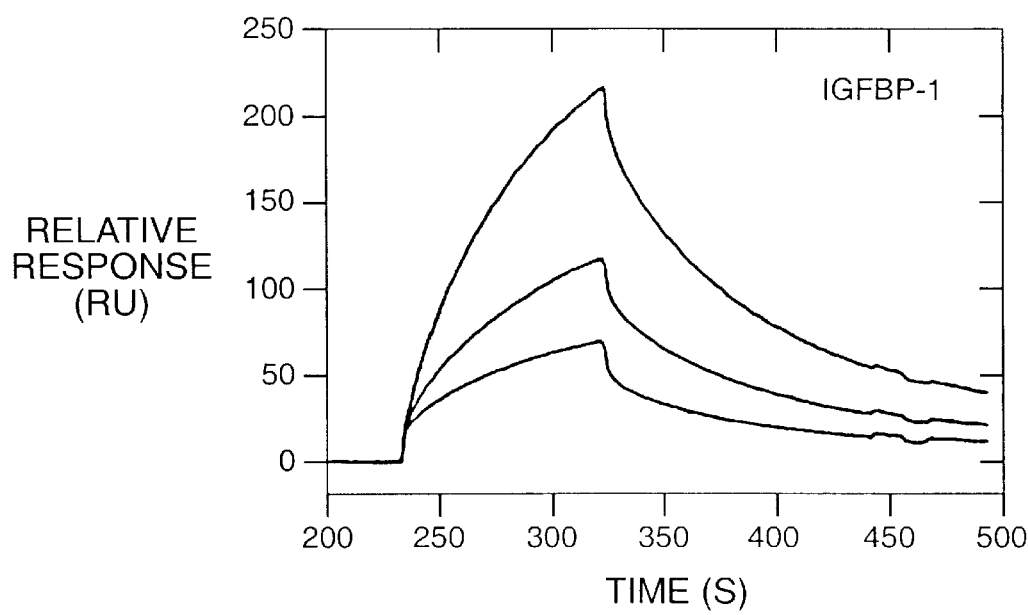
FIG._5C
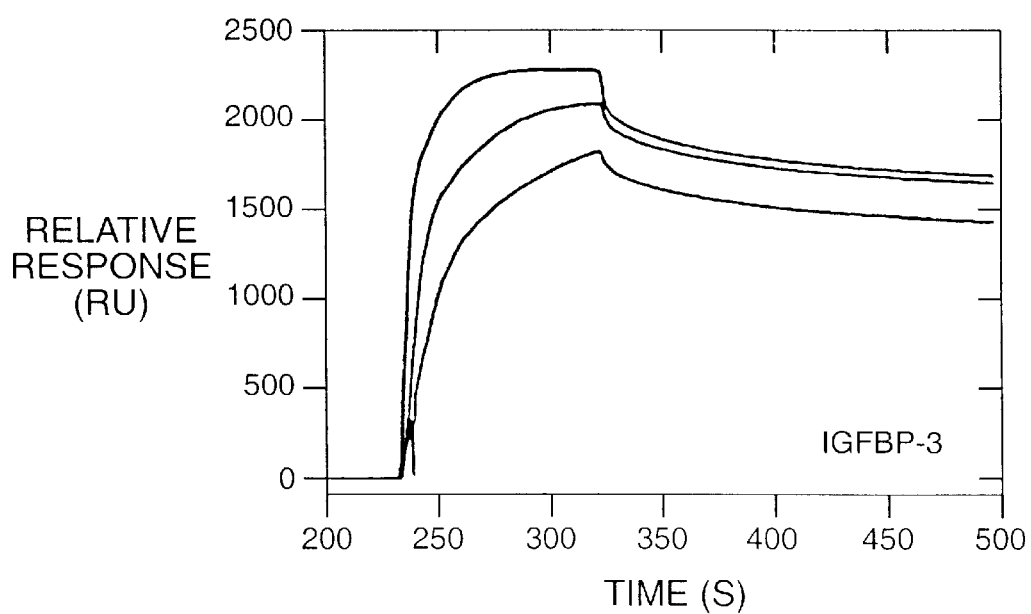
FIG._5D

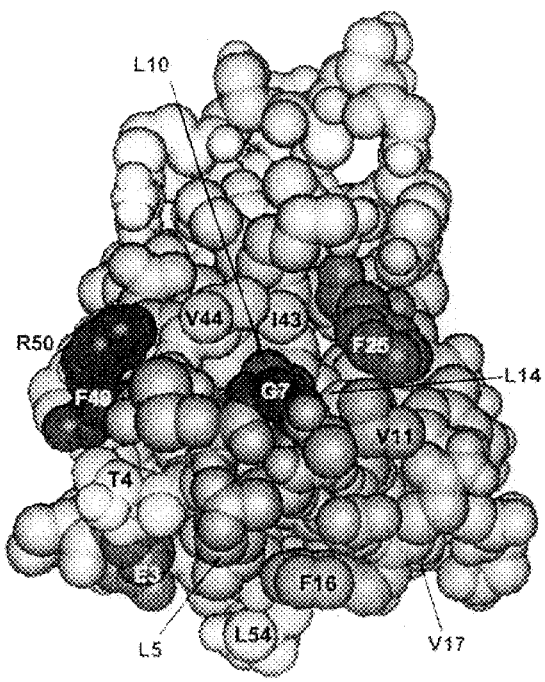
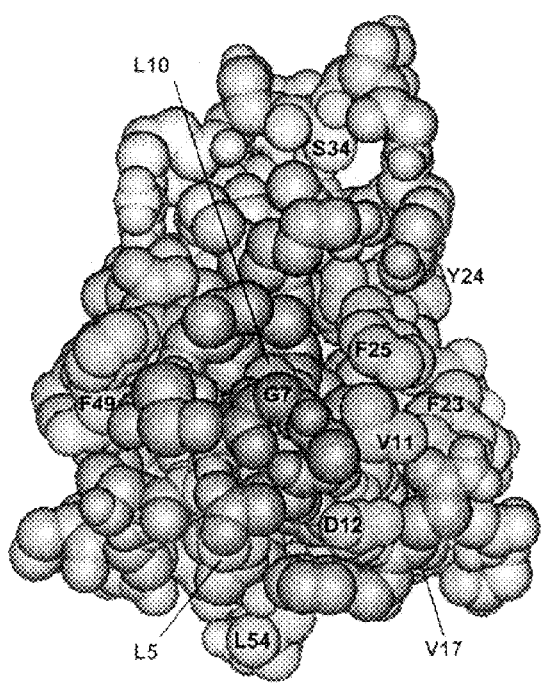
FIG._6A  FIG._6B

SEQUENCE LISTING

```
<160> NUMBER OF SEQ ID NOS: 6

<210> SEQ ID NO 1
<211> LENGTH: 70
<212> TYPE: PRT
<213> ORGANISM: Homo sapiens

<400> SEQUENCE: 1

Gly Pro Glu Thr Leu Cys Gly Ala Glu Leu Val Asp Ala Leu Gln
 1               5                  10                  15

Phe Val Cys Gly Asp Arg Gly Phe Tyr Phe Asn Lys Pro Thr Gly
                20                  25                  30

Tyr Gly Ser Ser Ser Arg Arg Ala Pro Gln Thr Gly Ile Val Asp
```

```
                    35                  40                  45

Glu Cys Cys Phe Arg Ser Cys Asp Leu Arg Arg Leu Glu Met Tyr
                50                  55                  60

Cys Ala Pro Leu Lys Pro Ala Lys Ser Ala
                65                  70
```

<210> SEQ ID NO 2
<211> LENGTH: 86
<212> TYPE: PRT
<213> ORGANISM: Homo sapiens

<400> SEQUENCE: 2

```
Phe Val Asn Gln His Leu Cys Gly Ser His Leu Val Glu Ala Leu
  1               5                  10                  15

Tyr Leu Val Cys Gly Glu Arg Gly Phe Phe Tyr Thr Pro Lys Thr
                 20                  25                  30

Arg Arg Glu Ala Glu Asp Leu Gln Val Gly Gln Val Glu Leu Gly
                 35                  40                  45

Gly Gly Pro Gly Ala Gly Ser Leu Gln Pro Leu Ala Leu Glu Gly
                 50                  55                  60

Ser Leu Gln Lys Arg Gly Ile Val Glu Gln Cys Cys Thr Ser Ile
                 65                  70                  75

Cys Ser Leu Tyr Gln Leu Glu Asn Tyr Cys Asn
                 80                  85  86
```

<210> SEQ ID NO 3
<211> LENGTH: 51
<212> TYPE: PRT
<213> ORGANISM: Homo sapiens

<400> SEQUENCE: 3

```
Phe Val Asn Gln His Leu Cys Gly Ser His Leu Val Glu Ala Leu
  1               5                  10                  15

Tyr Leu Val Cys Gly Glu Arg Gly Phe Phe Tyr Thr Pro Lys Thr
                 20                  25                  30

Gly Ile Val Glu Gln Cys Cys Thr Ser Ile Cys Ser Leu Tyr Gln
                 35                  40                  45

Leu Glu Asn Tyr Cys Asn
                 50  51
```

<210> SEQ ID NO 4
<211> LENGTH: 38
<212> TYPE: DNA
<213> ORGANISM: Artificial
<220> FEATURE:
<221> NAME/KEY: Artificial
<222> LOCATION: 1-38
<223> OTHER INFORMATION: Synthesized primer

<400> SEQUENCE: 4
agctgctttg atatgcatct cccgaaactc tgtgcggt                              38

<210> SEQ ID NO 5
<211> LENGTH: 37
<212> TYPE: DNA
<213> ORGANISM: Artificial
<220> FEATURE:
<221> NAME/KEY: Artificial
<222> LOCATION: 1-37
<223> OTHER INFORMATION: Synthesized primer

<400> SEQUENCE: 5

```
gagcgatctg ggtctagaca gatttagcgg gtttcag                                    37
```

<210> SEQ ID NO 6
<211> LENGTH: 24
<212> TYPE: DNA
<213> ORGANISM: Artificial
<220> FEATURE:
<221> NAME/KEY: Artificial
<222> LOCATION: 1-24
<223> OTHER INFORMATION: Synthesized oligonucleotide

<400> SEQUENCE: 6

```
aaaagggtat gtagaggttg aggt                                                  24
```

IGF-I POINT VARIANTS

This is a divisional Ser. No. 09/477,923 filed on Jan. 5, 2000, which claims priority to provisional application No. 60/115,010, filed on Jan. 6, 1999, which applications are incorporated.

BACKGROUND OF THE INVENTION

1. Field of Invention

This invention relates to molecules useful as agonists of the insulin-like growth factors (IGFs), as well as IGF-like insulin molecules. More particularly, these molecules inhibit the interaction of an IGF or insulin with one or more of the IGF binding proteins. Such molecules can be used, for example, in any methods where the IGFs or insulins are used, for example, in treating hyperglycemic, obesity-related, neurological, cardiac, renal, immunologic, and anabolic disorders.

2. Description of Background and Related Art

The insulin-like growth factors I and II (IGF-I and IGF-II, respectively) mediate multiple effects in vivo, including cell proliferation, cell differentiation, inhibition of cell death, and insulin-like activity (reviewed in Clark and Robinson, *Cytokine Growth Factor Rev.*, 7: 65–80 (1996); Jones and Clemmons, *Endocr. Rev.*, 16: 3–34 (1995)). Most of these mitogenic and metabolic responses are initiated by activation of the IGF-I receptor, an $\alpha_2\beta_2$-heterotetramer closely related to the insulin receptor (McInnes and Sykes, *Biopoly.*, 43: 339–366 (1997); Ullrich et al., *EMBO J.*, 5: 2503–2512 (1986)). Both proteins are members of the tyrosine kinase receptor superfamily and share common intracellular signaling cascades (Jones and Clemmons, supra). IGF-insulin hybrid receptors have been isolated, but their function is unknown. The IGF-I and insulin receptors bind their specific ligands with nanomolar affinity. IGF-I and insulin can cross-react with their respective non-cognate receptors, albeit at a 100–1000-fold lower affinity (Jones and Clemmons, supra). The crystal structure describing part of the extracellular portion of the IGF-I receptor has recently been reported (Garrett et al., *Nature*, 394: 395–399 (1998)).

Unlike insulin, the activity and half-life of IGF-I are modulated by six IGF-I binding proteins (IGFBP's 1–6), and perhaps additionally by a more distantly-related class of proteins (Jones and Clemmons, supra; Baxter et al., *Endocrinology*, 139: 4036 (1998)). IGFBP's can either inhibit or potentiate IGF activity, depending on whether they are soluble or cell-membrane associated (Bach and Rechler, *Diabetes Reviews*, 3: 38–61 (1995)). The IGFBPs bind IGF-I and IGF-II with varying affinities and specificities (Jones and Clemmons, supra; Bach and Rechler, supra). For example, IGFBP-3 binds IGF-I and IGF-II with a similar affinity, whereas IGFBP-2 and IGFBP-6 bind IGF-II with a much higher affinity than they bind IGF-I (Bach and Rechler, supra; Oh et al., *Endocrinology*, 132, 1337–1344 (1993)).

The classical IGFBP's have a molecular mass ranging from 22–31 kDa and contain a total of 16–20 cysteines in their conserved amino- and carboxy-terminal domains (Bach and Rechler, supra; Clemmons, *Cytokine Growth Factor Rev.*, 8: 45–62 (1997); Martin and Baxter, *Curr. Op. Endocrinol. Diab.*, 16–21 (1994)). The central domain connecting both cysteine-rich regions is only weakly conserved and contains the cleavage sites for IGFBP-specific proteases (Chernausek et al, *J. Biol. Chem.*, 270: 11377–11382 (1995); Clemmons, supra; Conover, *Prog. Growth Factor Res.*, 6: 301–309 (1995)). Further regulation of the IGFBP's may be achieved by phosphorylation and glycosylation (Bach and Rechler supra; Clemmons, supra). There is no high-resolution structure available for any intact member of the IGFBP family. However, the NMR structures of two N-terminal fragments from IGFBP-5 that retain IGF-binding activity have recently been reported (Kalus et al., *EMBO J.*, 17: 6558–6572 (1998)).

IGF-I is a single-chain 70-amino-acid protein with high homology to proinsulin. Unlike the other members of the insulin superfamily, the C region of the IGF's is not proteolytically removed after translation. The solution NMR structures of IGF-I (Cooke et al., *Biochemistry* 30: 5484–5491 (1991); Hua et al., *J. Mol. Biol.*, 259: 297–313 (1996)), mini-IGF-I (an engineered variant lacking the C-chain; DeWolf et al., *Protein Science*, 5: 2193–2202 (1996)), and IGF-II (Terasawa et al, *EMBO J.*, 13: 5590–5597(1994); Torres et al., *J. Mol. Biol.*, 248 385–401 (1995)) have been reported. It is generally accepted that distinct epitopes on IGF-I are used to bind receptor and binding proteins. It has been demonstrated in animal models that receptor-inactive IGF mutants are able to displace endogenous IGF-I from binding proteins and hereby generate a net IGF-I effect in vivo (Loddick et al., *Proc. Natl. Acad. Sci. USA*, 95: 1894–1898 (1998); Lowman et al., *Biochemistry*, 37: 8870–8878 (1998)) While residues Y24, Y29, Y31, and Y60 are implicated in receptor binding, IGF mutants thereof still bind to IGFBPs (Bayne et al, *J. Biol. Chem.*, 265: 15648–15652 (1990); Bayne et al, *J. Biol. Chem.*, 264: 11004–11008 (1989); Cascieri et al, *Biochemistry*, 27: 3229–3233 (1988); Lowman et al., supra.

Additionally, a variant designated (1–27,gly$^4$,38–70)-hIGF-I, wherein residues 28–37 of the C region human IGF-I are replaced by a four-residue glycine bridge, has been discovered that binds to IGFBP's but not to IGF receptors (Bar et al, *Endocrinology* 127: 3243–3245 (1990)).

A multitude of mutagenesis studies have addressed the characterization of the IGFBP-binding epitope on IGF-I (Bagley et al., *Biochem.J.*, 259: 665–671 (1989); Baxter et al., *J. Biol. Chem.*,267: 60–65(1992); Bayne et al., *J. Biol. Chem.*, 263: 6233–6239 (1988); Clemmons et al., *J. Biol. Chem.*, 265: 12210–12216 (1990); Clemmons et al., *Endocrinology*, 131: 890–895 (1992); Oh et al., supra). In summary, the N-terminal residues 3 and 4 and the helical region comprising residues 8–17 were found to be important for binding to the IGFBP's. Additionally, an epitope involving residues 49–51 in binding to IGFBP-1, -2 and -5 has been identified (Clemmons et al., *Endocrinology*, supra, 1992). Furthermore, a naturally occurring truncated form of IGF-I lacking the first three N-terminal amino acids (called des(1–3)-IGF-I) was demonstrated to bind IGFBP-3 with 25 times lower affinity(Heding et al, *J. Biol. Chem.*, 271: 13948–13952 (1996); U.S. Pat. Nos. 5,077,276; 5,164,370; 5,470,828).

In an attempt to characterize the binding contributions of exposed amino acid residues in the N-terminal helix, several alanine mutants of IGF-I were constructed (Jansson et al., *Biochemistry*, 36: 4108–4117 (1997)). However, the circular dichroism spectra of these mutant proteins showed structural changes compared to wild-type IGF-I, making it difficult to clearly assign IGFBP-binding contributions to the mutated side chains. A different approach was taken in a very recent study where the IGFBP-1 binding epitope on IGF-I was probed by heteronuclear NMR spectroscopy (Jansson et al., *J. Biol. Chem.*, 273: 24701–24707 (1998)). The authors additionally identified residues R36, R37 and R50 to be functionally involved in binding to IGFBP-1.

Other IGF-I variants have been disclosed. For example, in the patent literature, WO 96/33216 describes a truncated variant having residues 1–69 of authentic IGF-I. EP 742,228 discloses two-chain IGF-I superagonists which are derivatives of the naturally occurring single-chain IGF-I having an abbreviated C domain. The IGF-I analogs are of the formula: BC"-A wherein B is the B domain of IGF-I or a functional analog thereof, C is the C domain of IGF-I or a functional analog thereof, n is the number of amino acids in the C domain and is from about 6 to about 12, and A is the A domain of IGF-I or a functional analog thereof.

Additionally, Cascieri et al., *Biochemistry*, 27: 3229–3233 (1988) discloses four mutants of IGF-I, three of which have reduced affinity to the Type 1 IGF receptor. These mutants are: $(Phe^{23}, Phe^{24}, Tyr^{25})$IGF-I (which is equipotent to human IGF-I in its affinity to the Types 1 and 2 IGF and insulin receptors), $(Leu^{24})$IGF-I and $(Ser^{24})$IGF-I (which have a lower affinity than IGF-I to the human placental Type 1 IGF receptor, the placental insulin receptor, and the Type 1 IGF receptor of rat and mouse cells), and desoctapeptide $(Leu^{24})$IGF-I (in which the loss of aromaticity at position 24 is combined with the deletion of the carboxyl-terminal D region of hIGF-I, which has lower affinity than $(Leu^{24})$IGF-I for the Type 1 receptor and higher affinity for the insulin receptor). These four mutants have normal affinities for human serum binding proteins.

Bayne et al., *J. Biol. Chem.*, 264: 11004–11008 (1988) discloses three structural analogs of IGF-I: (1–62)IGF-I, which lacks the carboxyl-terminal 8-amino-acid D region of IGF-I; (1–27,$Gly^4$,38–70)IGF-I, in which residues 28–37 of the C region of IGF-I are replaced by a four-residue glycine bridge; and (1–27,$Gly^4$,38–62) IGF-I, with a C region glycine replacement and a D region deletion. Peterkofsky et al., *Endocrinology*, 128: 1769–1779 (1991) discloses data using the $Gly^4$ mutant of Bayne et al., supra, Vol. 264. U.S. Pat. No. 5,714,460 refers to using IGF-I or a compound that increases the active concentration of IGF-I to treat neural damage.

Cascieri et al., *J. Biol. Chem.*, 264: 2199–2202 (1989) discloses three IGF-I analogs in which specific residues in the A region of IGF-I are replaced with the corresponding residues in the A chain of insulin. The analogs are: ($Ile^{41}$, $Glu^{45}$,$Gln^{46}$,$Thr^{49}$,$Ser^{50}$,$Ile^{51}$,$Ser^{53}$,$Tyr^{55}$,$Gln^{56}$)IGF-I, an A chain mutant in which residue 41 is changed from threonine to isoleucine and residues 42–56 of the A region are replaced; ($Thr^{49}$,$Ser^{50}$,$Ile^{51}$)IGF-I; and ($Tyr^{55}$, $Gln^{56}$) IGF-I.

WO 94/04569 discloses a specific binding molecule, other than a natural IGFBP, that is capable of binding to IGF-I and can enhance the biological activity of IGF-I. WO98/45427 published Oct. 15,1998 and Lowman et al., supra, disclose IGF-I agonists identified by phage display. Also, WO 97/39032 discloses ligand inhibitors of IGFBP's and methods for their use.

There are various forms of human insulin on the market that differ in the duration of action and onset of action, but have the native human sequence. Jens Brange, *Galenics of Insulin, The Physico-chemical and Pharmaceutical Aspects of Insulin and Insulin Preparations* (Springer-Verlag, New York, 1987), page 17–40. Regular insulin is a clear neutral solution that contains hexameric insulin. It is short acting, its onset of action occurs in 0.5 hour after injection and duration of action is about 6–8 hours. NPH (Neutral Protamine Hagedorn) insulin, also called Isophane Insulin, is a crystal suspension of insulin-protamine complex. These crystals contain approximately 0.9 molecules of protamine and two zinc atoms per insulin hexamer. Dodd et al.,*Pharmaceutical Research*, 12: 60–68 (1995). NPH-insulin is an intermediate-acting insulin; its onset of action occurs in 1.5 hours and its duration of action is 18–26 hours. 70/30 insulin is composed of 70% NPH-insulin and 30% Regular insulin. There are also Semilente insulin (amorphous precipitate of zinc insulin complex), UltraLente insulin (zinc insulin crystal suspension), and Lente insulin (a 3:7 mixture of amorphous and crystalline insulin particles). Of the various types of insulins available, NPH-, 70/30, and Regular insulin are the most widely used insulins, accounting for 36%, 28%, and 15%, respectively, of the insulin prescriptions in 1996.

The use of recombinant DNA technology and peptide chemistry have allowed the generation of insulin analogs with a wide variety of amino acid substitutions, and IGF-like modifications to insulin have been made for the purpose of modifying insulin pharmacokinetics (Brange et al., *Nature*, 333: 679 (1988); Kang et al., *Diabetes Care*, 14: 571 (1991); DiMarchi et al., "Synthesis of a fast-acting insulin analog based upon structural homology with insulin-like growth factor-I," in: *Peptides: Chemistry and Biology*, Proceedings of the Twelfth American Peptide Symposium, J. A. Smith and J. E. Rivier, eds. (ESCOM, Leiden, 1992), pp. 26–28; Weiss et al., *Biochemistry*,30: 7373 (1991); Howey et al., *Diabetes*, 40: (Supp 1) 423A (1991); Slieker and Sundell, *Diabetes*, 40: (Supp 1) 168A (1991); Cara et al., *J. Biol. Chem.*,265: 17820 (1990); Wolpert et al., *Diabetes*, 39: (Supp 1) 140A (1990); Bornfeldt et al., *Diabetologia*, 34: 307 (1991); Drejer, *Diabetes/Metabolism Reviews*, 8: 259 (1992); Slieker et al., *Adv. Experimental Med. Biol.*, 343: 25–32 (1994)). One example of such an insulin analog is Humalog™ insulin (rapid-acting monomeric insulin solution, as a result of reversing the Lys (B28) and Pro(B29) amino acids on the insulin B-chain) that was recently introduced into the market by Eli Lilly and Company. A review of the recent insulin mutants in clinical trials and on the market is found in Barnett and Owens, *Lancet*, 349: 47–51 (1997).

Slieker et al., 1994, supra, describe the binding affinity of various IGF and insulin variants to IGFBPs, IGF receptor, and insulin receptor, and in particular sought to confer IGFBP-binding ability to insulin through several combinations of mutations, including: ($Phe^{38}$, $Arg^{39}$, $Ser^{40}$) insulin, ($Glu^4$, Gln16, $Phe^{17}$) insulin, and ($Glu^4$, $Gln^{16}$, $Phe^{17}$, $Phe^{38}$, $Arg^{39}$, $Ser^{40}$) insulin (the numbering of mature insulin used herein consists of consecutive numbering in the B chain (residues 1–30), followed by consecutive numbering in the A chain (residues 31–51); these correspond to residues numbered 1–30 and residues 66–86, respectively of proinsulin; cf. FIG. 4 herein). However, only weak affinity was found for these variants binding to the IGF binding proteins and insulin-receptor affinity was reduced as compared with wild-type insulin (Slieker et al., supra).

Although earlier reports could not find any affinity of insulin for the binding proteins, a group has measured a weak affinity of 251+/–91 nM of insulin for IGFBP-3 by BIAcore™ experiments (Heding et al., supra).

Despite all these efforts, the view of the IGFBP-binding epitope on IGF-I has remained diffuse and at low resolution. The previous studies most often involved insertions of homologous insulin regions into IGF-I or protein truncations (e. g. des(1–3)-IGF-I), not differentiating between effects attributed to misfolding and real binding determinants. Combining the results of all these studies is further complicated by the fact that different techniques were used to analyze complex formation of the mutant IGF forms with the IGFBP's, ranging from radiolabeled ligand binding assays to biosensor analysis.

There is a need in the art for molecules that act as IGF or insulin agonists, and also for molecules that binds to IGF binding proteins with high affinity and specificity for therapeutic or diagnostic purposes.

SUMMARY OF THE INVENTOION

Accordingly, in one embodiment, the invention provides an IGF-I variant wherein an amino acid at position 3, 4, 5, 7, 10, 14, 17, 23, 24, 25, 43, 49 or 63, or any of such amino acids in combination with an amino acid at position 12 or 16 or both 12 and 16 of native-sequence human IGF-I, or any combination thereof, is replaced with any amino acid at said position 7 or with an alanine, a glycine, or a serine residue at any position other than said position 7.

In one preferred embodiment, the amino acids at said positions 16 and 49 are replaced to obtain binders to IGFBP-3. Another preferred embodiment for obtaining binders to IGFBP-3 is a variant containing mutations at positions 3 and 7.

In a still further preferred embodiment, additionally tyrosine at said position 24 is replaced with leucine or tyrosine at said position 31 is replaced with alanine or both are replaced, to disrupt or prevent receptor binding. Most preferably, both tyrosines at said positions 24 and 31 are replaced.

In another embodiment, the invention provides a long-half-life IGF-like insulin wherein phenylalanine at position 1 of native-sequence human pro-insulin is deleted (des(1)-proinsulin), or glutamine at position 4 of native-sequence human pro-insulin is replaced with glutamic acid, or leucine at position 17 of native-sequence human pro-insulin is replaced with phenylalanine, or phenylalanine at position 25 of native-sequence human pro-insulin is replaced with tyrosine, or tyrosine at position 26 of native-sequence human pro-insulin is replaced with phenylalanine, or threonine at position 73 of native-sequence human pro-insulin is replaced with phenylalanine, or any combination thereof.

Preferably, for the IGF-like insulin, amino acids at said positions 4, 17, 26, and/or 73 are replaced to generate IGFBP-1-specific mutants, or the amino acid at position 1 is deleted and the amino acids at positions 25, 26, and/or 73 are replaced to generate IGFBP-3-specific mutants.

In yet another embodiment, the invention provides an IGF-like insulin wherein the phenylalanine at position 1 is deleted (des(1)-insulin), or glutamine at position 4 of native-sequence human mature insulin is replaced with glutamic acid, or leucine at position 17 of native-sequence human mature insulin is replaced with phenylalanine, or phenylalanine at position 25 of native-sequence human mature insulin is replaced with tyrosine, or tyrosine at position 26 of native-sequence human mature insulin is replaced with phenylalanine, or threonine at position 38 of native-sequence human mature insulin is replaced with phenylalanine, or any combination thereof (Note: the numbering of mature insulin used here consists of consecutive numbering in the B chain (residues 1–30), followed by consecutive numbering in the A chain (residues 31–51)).

In a preferred embodiment, amino acids of the above mature insulin at positions 4, 17, 26, and 38 are replaced, to create a mutant that is IGFBP-1 specific.

In another preferred embodiment, the amino acid at position 1 of the above mature insulin is deleted, and amino acids of the above mature insulin at positions 25, 26, and 38 are replaced, to create a mutant that is IGFBP-3 specific.

Also provided herein is a composition comprising one of the peptides described above in a carrier, preferably a pharmaceutically acceptable carrier. Preferably, this composition is sterile.

Uses of these peptides include all uses that liberate or enhance at least one biological activity of exogenous or endogenous IGFs or insulin. They can be used in treating, inhibiting, or preventing conditions in which an IGF such as IGF-I or insulin is useful, i.e., in treating an IGF disorder or an insulin disorder by administering an effective amount of the peptide to a mammal, as described below.

Additionally provided herein is a method for increasing serum and tissue levels of biologically active IGF or insulin in a mammal comprising administering to the mammal an effective amount of a peptide as described above. The mammal is preferably human. Also preferred is where administering the peptide, if it is mimicking IGF-I, preferably in an amount effective to produce body weight gain, causes an increase in anabolism in the mammal. Additionally preferred is that glycemic control is effected in the mammal after the peptide is administered.

The peptide herein can be administered alone or together with another agent such as GH, a GH-releasing peptide (GHRP), a GH-releasing factor (GHRF), a GH-releasing hormone (GHRH),a GH secretagogue, an IGF, an IGF in combination with an IGFBP, an IGFBP, GH in combination with a GH binding protein (GHBP), insulin, or a hypoglycemic agent (which includes in the definition below an insulin-sensitizing agent such as thiazolidinedione).

In yet another aspect of the invention, a method is provided for effecting glycemic control in a mammal comprising administering to the mammal an effective amount of one or more of the above peptides. Preferably, the peptide also reduces plasma insulin secretion and blood glucose levels in a mammal. Also preferably, the mammal has a hyperglycemic disorder such as diabetes. This method can additionally comprise administering to the mammal an effective amount of a hypoglycemic agent or insulin.

Also provided is a method for increasing serum and tissue levels of biologically active IGF in a mammal, or a method for increasing anabolism in a mammal, or a method for controlling glycemia in a mammal comprising administering to the mammal an effective amount of the composition containing the peptide herein.

Also contemplated herein is a kit comprising a container containing a pharmaceutical composition containing the peptide herein and instructions directing the user to utilize the composition. This kit may optionally further comprise a container containing a GH, a GHRP, a GHRF, a GHRH, a GH secretagogue, an IGF, an IGF complexed to an IGFBP, an IGFBP, a GH complexed with a GHBP, insulin, or a hypoglycemic agent.

For an identification of the peptides herein, human IGF-I was displayed monovalently on filamentous phagemid particles (U.S. Pat. Nos. 5,750,373 and 5,821,047), and a complete alanine-scanning mutagenesis thereof (Cunningham and Wells, Science, 244: 1081–1085 (1989); U.S. Pat. No. 5,834,250) was performed by phage display ("turbo-ala scan") (Cunningham et al., EMBO J., 13: 2508–2515 (1994); Lowman, Methods Mol. Biol., 87: 249–264 (1998)). The mutant IGF-phagemids were used to map the binding determinants on IGF-I for IGFBP-1 and IGFBP-3. The alanine scanning reveals specificity determinants for these binding proteins, so as to generate binding-protein-specific IGF variants or insulin variants that bind specifically to IGFBP-1 or IGFBP-3 to modulate their clearance half-life, improve proteolytic stability, or alter their tissue distribution in vivo. These mutants should also be useful for mapping the functional binding site for IGF receptor, whose crystal structure was recently reported (Garrett et al., supra). In addition, it may be of interest to map the epitopes of various IGF-binding antibodies or of other peptides or proteins that bind to IGF-I.

BRIEF DESCRIPTION OF THE DRAWINGS

FIGS. 1A and 1B show a phage ELISA of the variant, G1S-A70V IGF-I, binding to IGFBP-1 (FIG. 1A) and IGFBP-3 (FIG. 1B). Microtiter plates coated with 1 μg/ml IGFBP-1 (FIG. 1A) or IGFBP-3 (FIG. 1B) were incubated with phage particles displaying G1S-A70V in the presence of the indicated amounts of soluble competitor protein, IGFBP-1 (FIG. 1A) or IGFBP-3 (FIG. 1B). The half-maximal inhibitory concentration ($IC_{50}$) of competitor, i.e., the inhibitory concentration of competitor that resulted in half-maximal binding of the phagemid in that particular experiment, is denoted for the respective IGFBP.

FIGS. 2A and 2B show the loss or gain of IGFBP affinity for the IGF-I mutants tested by phage ELISA. Relative $IC_{50}$ values ($IC_{50mut}/IC_{50\ G1S-A70V}$) of each IGF-I alanine mutant (affinity changes of each mutant for the binding proteins with respect to IGF-I G1S-A70V) are shown for IGFBP-1 (filled bars) and IGFBP-3 (open bars). Data are taken from Table I below. Relative $IC_{50}$ values <1 denote gain of affinity; values >1 denote loss of affinity. The asterisk indicates that these particular variants were not displayed on phage, as judged by antibody binding.

FIGS. 3A and 3B show binding specificity of the IGF-I variant F49A displayed on phage to IGFBP-1 and -3, respectively, in competitive-phage ELISA. Phagemid particles displaying F49A (squares) were bound to plates coated with IGFBP-3 in the presence of the indicated amounts of soluble IGFBP-1 (FIG. 3A) or IGFBP-3 (FIG. 3B). The same experiment was carried out in parallel with phage displaying the wild-type-like IGF-I variant G1S-A70V (circles). See Tables I and II below for absolute $IC_{50}$ values. Data points are mean±standard deviation, n=2. Immunosorbent plates were coated with 1 μg/ml IGFBP-3 and ELISA were carried out as described in the Examples below using wild-type IGF-I phage (WT, circles) and IGF-F49A phage (F49A, squares) in parallel. Experiments were carried out in duplicate, and data points are shown as mean±standard deviation. The $IC_{50}$ values of the actual experiment are indicated in the figure.

FIG. 4 discloses a sequence alignment of native-sequence human IGF-I (designated wtIGF)(SEQ ID NO:1), native-sequence human proinsulin (designated proinsulin) (SEQ ID NO:2), and native-sequence human insulin (designated insulin (B chain) followed by insulin (A chain)) (SEQ ID NO:3). The asterisks and dots indicate sequence identity and sequence similarity, respectively, at the indicated amino acid positions among the three sequences.

FIGS. 5A–5D show a biosensor analysis of IGFBP binding to immobilized IGF-1 variants. Sensorgrams are shown for IGFBP-1 (FIGS. 5A, 5C) or IGFBP-3 (FIGS. 5B, 5D) binding to immobilized wild-type IGF-I (FIGS. 5A, 5B) or F49A IGF variant (FIGS. 5C, 5D). The concentrations of ligand in each experiment were 1 μM, 500 nM, and 250 nM. See Table II for kinetic parameters.

FIGS. 6A–6B show a model of the functional binding epitopes for IGFBP-1 and IGFBP-3, respectively, on the surface of IGF-1. Amino acid side chains were classified according to their relative contribution in binding energy (Table I) and colored as follows: no effect (grey); 2–5 fold loss of apparent affinity (yellow); 5–10 fold (orange); 10–100 fold (bright red); >100 fold (dark red). If available, numbers from phage ELISA experiments in Table I below were used. BIAcore™ data were used instead for V11A, R36A, and P39A variants (Table II). The NMR structure of IGF-I (Cooke et al., supra) was represented using the program Insight II™ (MSI, San Diego, Calif.). The binding epitope for IGFBP-1 (FIG. 6A) is located on the "upper" and "lower" face of the N-terminal helix (residues 8–17), connected by the energetically-important residue F49. For IGFBP-3 (FIG. 6B), individual IGF-I side chains contribute very little binding energy. The binding epitope has shifted away from the N-terminus and newly includes G22, F23, Y24.

DESCRIPTION OF THE PREFERRED EMBODIMENTS

A. Definitions

As used herein, "mammal" for purposes of treatment refers to any animal classified as a mammal, including humans, domestic, and farm animals, and zoo, sports, or pet animals, such as dogs, horses, cats, sheep, pigs, cows, etc. The preferred mammal herein is a human. The term "non-adult" refers to mammals that are from perinatal age (such as low-birth-weight infants) up to the age of puberty, the latter being those that have not yet reached full growth potential.

As used herein, "IGF" refers to native insulin-like growth factor-I and native insulin-like growth factor-II as well as natural variants thereof such as brain IGF, otherwise known as des(1–3)IGF-I.

As used herein, "IGF-I" refers to insulin-like growth factor-I from any species, including bovine, ovine, porcine, equine, and human, preferably human, and, if referring to exogenous administration, from any source, whether natural, synthetic, or recombinant. "Native-sequence" human IGF-I, the sequence of which is shown in FIG. 4 (SEQ ID NO:1), is prepared, e.g., by the process described in EP 230,869 published Aug. 5, 1987; EP 128,733 published Dec. 19, 1984; or EP 288,451 published Oct. 26,1988. More preferably, this native-sequence IGF-I is recombinantly produced and is available from Genentech, Inc., South San Francisco, Calif. for clinical investigations.

As used herein, "IGF-II" refers to insulin-like growth factor-II from any species, including bovine, ovine, porcine, equine, and human, preferably human, and, if referring to exogenous administration, from any source, whether natural, synthetic, or recombinant. It may be prepared by the method described in, e.g. EP 128,733.

An "IGFBP" or an "IGF binding protein" refers to a protein or polypeptide normally associated with or bound or complexed to IGF-I or IGF-II, whether or not it is circulatory (i.e., in serum or tissue). Such binding proteins do not include receptors. This definition includes IGFBP-1, IGFBP-2, IGFBP-3, IGFBP-4, IGFBP-5, IGFBP-6, Mac 25 (IGFBP-7), and prostacyclin-stimulating factor (PSF) or endothelial cell-specific molecule (ESM-1), as well as other proteins with high homology to IGFBPs. Mac 25 is described, for example, in Swisshelm et al., *Proc. Natl. Acad. Sci. USA,* 92: 4472–4476 (1995) and Oh et al.,*J: Biol. Chem.,* 271: 30322–30325 (1996). PSF is described in Yamauchi et al., *Biochemical Journal,* 303: 591–598 (1994). ESM-1 is described in Lassalle et al., *J. Biol. Chem.* 271: 20458–20464(1996). For other identified IGFBPs, see, e.g., EP 375,438 published Jun. 27, 1990; EP 369,943 published May 23, 1990; WO 89/09268 published Oct. 5, 1989; Wood et al., *Molecular Endocrinology,* 2: 1176–1185 (1988); Brinkman et al., *The EMBO J.,* 7: 2417–2423 (1988); Lee et al., *Mol. Endocrinol.,* 2: 404–411 (1988); Brewer et al., *BBRC,* 152: 1289–1297 (1988); EP294,021 published Dec. 7, 1988; Baxter et al., *BBRC,* 147: 408–415 (1987); Leung et al, *Nature*, 330: 537–543 (1987); Martin et al., *J. Biol. Chem.*, 261: 8754–8760(1986); Baxter et al, *Comp. Biochem. Physiol.*, 91B: 229–235 (1988); WO 89/08667 published Sep. 21, 1989; WO 89/09792 published Oct. 19, 1989; and Binkert et al., *EMBO J.*, 8: 2497–2502 (1989).

The term "body fluid" refers to a biological sample of liquid from a mammal, preferably from a human. Such fluids include aqueous fluids such as serum, plasma, lymph fluid, synovial fluid, follicular fluid, seminal fluid, amniotic fluid, milk, whole blood, urine, cerebrospinal fluid, saliva, sputum, tears, perspiration, mucus, tissue culture medium, tissue extracts, and cellular extracts.

As used herein, "human IGF receptor" refers to any receptor for an IGF found in humans and includes the Type 1 and Type 2 IGF receptors in humans to which both human IGF-I and IGF-II bind, such as the placental Type 1 IGF-I receptor, etc.

"Peptides" include an IGF-I agonist, IGF-I variant, insulin agonist, insulin variant, or IGF-like insulin having at least two amino acids and include polypeptides having at least about 50 amino acids. The definition includes peptide derivatives, their salts, or optical isomers.

As used herein, "insulin" refers to any form of insulin from any species, and whether natively or synthetically or recombinantly derived. It maybe formulated, for example, as Regular insulin, NPH insulin, 70/30 insulin, Semilente insulin, UltraLente insulin, or Lente insulin. If an insulin is to be administered together with an IGF-like insulin or IGF-I variant herein, it is preferably Regular insulin, NPH insulin, 70/30 insulin, or HUMALOG™ brand insulin.

"Proinsulin" refers to insulin that contains the A, B, and C peptide, the native sequence of which is shown in FIG. 4 (SEQ ID NO:2). Conversion of proinsulin to "mature insulin" occurs by excision of the region from R31 to R65. The resulting amino-terminal peptide of mature insulin is called B-chain, and the carboxy-terminal peptide A-chain. The chains are held together by two inter-chain disulfides. Mature insulin is a soluble protein. The numbering for mature insulin variants herein consists of consecutive numbering in the B chain (residues 1–30), followed by consecutive numbering in the A chain (residues 31–51). "Native-sequence" human proinsulin has the sequence (SEQ ID NO:2) shown in FIG. 4, and "native-sequence" human mature insulin has the sequence (SEQ ID NO:3) shown in FIG. 4.

"IGF-like insulin" is a peptide that simulates at least one of the biological activities of IGF-I, including those biological activities listed under "IGF disorder" and under Modes below. Preferably, such IGF-like insulin is long-acting.

An "IGF disorder" is any condition that would benefit from treatment with an IGF, including but not limited to, for example, lung diseases, hyperglycemic disorders as set forth below, renal disorders, such as acute and chronic renal insufficiency, end-stage chronic renal failure, glomerulonephritis, interstitial nephritis, pyelonephritis, glomerulosclerosis, e.g., Kimmelstiel-Wilson in diabetic patients and kidney failure after kidney transplantation, obesity, GH-insufficiency, Turner's syndrome, Laron's syndrome, short stature, undesirable symptoms associated with aging such as obesity and increased fat mass-to-lean ratios, immunological disorders such as immunodeficiencies including decreased CD4 counts and decreased immune tolerance or chemotherapy-induced tissue damage, bone marrow transplantation, diseases or insufficiencies of cardiac structure or function such as heart dysfunctions and congestive heart failure, neuronal, neurological, or neuromuscular disorders, e.g., peripheral neuropathy, multiple sclerosis, muscular dystrophy, or myotonic dystrophy, and catabolic states associated with wasting caused by any condition, including, e.g., trauma or wounding or infection such as with a bacterium or human virus such as HIV, wounds, skin disorders, gut structure and function that need restoration, and so forth. The IGF disorder being treated may be a combination of two or more of the above disorders. The preferred disorders targeted for treatment herein are diabetes and obesity, heart dysfunctions, kidney disorders, neurological disorders, whole body growth disorders, and immunological disorders.

An "insulin disorder" is a condition that would benefit from treatment with an insulin, such as hyperglycemic disorders.

As used herein, the term "hyperglycemic disorders" refers to all forms of diabetes and disorders resulting from insulin resistance, such as Type I and Type II diabetes, as well as severe insulin resistance, hyperinsulinemia, and hyperlipidemia, e.g., obese subjects, and insulin-resistant diabetes, such as Mendenhall's Syndrome, Werner Syndrome, leprechaunism, lipoatrophic diabetes, and other lipoatrophies. The preferred hyperglycemic disorder is diabetes, especially Type 1 and Type II diabetes. "Diabetes" itself refers to a progressive disease of carbohydrate metabolism involving inadequate production or utilization of insulin and is characterized by hyperglycemia and glycosuria.

As used herein, the term "treating" refers to both therapeutic treatment and prophylactic or preventative measures. Those in need of treatment include those already with the disorder as well as those prone to having the disorder or diagnosed with the disorder or those in which the disorder is to be prevented. Consecutive treatment or administration refers to treatment on at least a daily basis without interruption in treatment by one or more days. Intermittent treatment or administration, or treatment or administration in an intermittent fashion, refers to treatment that is not consecutive, but rather cyclic in nature. The treatment regime herein can be either consecutive or intermittent.

As used herein, the term "hypoglycemic agent" refers to compounds that are useful for regulating glucose metabolism, preferably oral agents. More preferred herein for human use are insulin and the sulfonylurea class of oral hypoglycemic agents, which cause the secretion of insulin by the pancreas. Examples include glyburide, glipizide, and gliclazide. In addition, agents that enhance insulin sensitivity or are insulin sensitizing, such as biguanides (including metformin and phenformin) and thiazolidenediones such as REZULIN™ (troglitazone) brand insulin-sensitizing agent, and other compounds that bind to the PPARγ nuclear receptor, are within this definition, and also are preferred.

As used herein, "active" or "biologically active" IGF in the context of changing serum and tissue levels of endogenous IGF refers to IGF that binds to its receptor or otherwise causes a biological activity to occur, such as those biological activities of endogenous or exogenous IGF referred to herein.

"Growth-hormone-releasing peptides or factors" ("GHRP" or "GHRF") are described below, as are secretagogues. A "growth-hormone-releasing hormone" ("GHRH") can be any hormone that releases GH from the cells or tissue. "Growth hormone in combination with a growth hormone binding protein" ("GH" plus "GHBP") means a GH complexed with or otherwise associated with one of its binding proteins. Similarly, "IGF in combination with an IGF binding protein" ("IGF" plus "IGFBP") refers to an IGF complexed with or otherwise associated with one of its IGFBPs.

B. Modes for Carrying Out the Invention

The invention herein relates, in one aspect to an IGF-I variant wherein one or more amino acids of native-sequence human IGF-I at selected positions are replaced. Specifically, one or more amino acids at positions 3, 4, 5, 7, 10, 14, 17, 23, 24, 25, 43, 49 and/or 63, or one or more amino acids at the above positions along with one or both amino acids at positions 12 and/or 16, are replaced The replacement at position 7 is with any amino acid residue, and the replacement at any position other than position 7 is with either an alanine, a glycine, or a serine residue. Preferably, the amino acids in question are replaced by an alanine, glycine, or serine.

One preferred variant has the amino acids at positions 16 and 49 replaced Another preferred variant has amino acids at positions 3 and 7 replaced. Preferably, the amino acids at positions 49 and 63 are not singly replaced.

In another preferred embodiment, the variant additionally has its tyrosine at position 24 replaced with leucine or its tyrosine at position 31 replaced with alanine. Most preferably, both tyrosine residues are replaced.

The invention additionally provides, in another aspect, two types of IGF-like insulins. In one such embodiment, the phenylalanine at position I of native-sequence human pro-insulin is deleted, or the glutamine at position 4 of native-sequence human pro-insulin is replaced with glutamic acid, or leucine at position 17 of native-sequence human pro-insulin is replaced with phenylalanine, or phenylalanine at position 25 of native-sequence human proinsulin is replaced with tyrosine, or tyrosine at position 26 of native-sequence human pro-insulin is replaced with phenylalanine, or threonine at position 73 of native-sequence human pro-insulin is replaced with phenylalanine, or any combination thereof is made.

Preferred combinations are those wherein amino acids at said positions 4 and 17 are replaced, or wherein amino acids at said positions 4 and 26 are replaced, or wherein amino acids at said positions 4 and 73 are replaced, or wherein amino acids at said positions 17 and 26 are replaced, or wherein amino acids at said positions 26 and 73 are replaced, or wherein amino acids at said positions 17 and 73 are replaced, or wherein amino acids at said positions 4, 17, and 26 are replaced, or wherein amino acids at said positions 4, 26, and 73 are replaced, or wherein amino acids at said positions 4, 17, and 73 are replaced, or wherein amino acids at said positions 17, 26, and 73 are replaced, or wherein the amino acid at position 1 is deleted and the amino acid at said position 25 is replaced, or wherein the amino acid at position 1 is deleted and the amino acid at said position 26 is replaced, or wherein the amino acid at position 1 is deleted and the amino acid at said position 73 is replaced, or wherein the amino acid at position 1 is deleted and the amino acids at said positions 25 and 26 are replaced, or wherein the amino acid at position 1 is deleted and the amino acids at said positions 25 and 73 are replaced, or wherein the amino acid at position 1 is deleted and the amino acids at said positions 26 and 73 are replaced, or wherein the amino acid at position 1 is deleted and the amino acids at said positions 25, 26, and 73 are replaced.

Most preferred is the variant wherein amino acids at said positions 4, 17, 26, and 73 are replaced, to be IGFBP-1-selective, or wherein the amino acid at position 1 is deleted and the amino acids at said positions 25, 26, and 73 are replaced, to be IGFBP-3-selective.

The other type of IGF-like insulin is based on soluble mature insulin. In this case the same mutations are made as above for pro-insulin, but the numbering is changed in certain cases. Hence, glutamine at position 4 of native-sequence human mature insulin is replaced with glutamic acid, or leucine at position 17 of native-sequence human mature insulin is replaced with phenylalanine, or phenylalanine at position 25 of native-sequence human mature insulin is replaced by tyrosine, or tyrosine at position 26 of native-sequence human mature insulin is replaced with phenylalanine, or threonine at position 38 of native-sequence human mature insulin is replaced with phenylalanine, or any combination thereof is made.

For IGFBP-1-selective mutants amino acids at said positions 4, 17, 26, and 38 are replaced, and for IGFBP-3-selective mutants, the amino acid at position 1 is deleted and the amino acids at said positions 25, 26, and 38 are replaced.

The peptides of this invention can be made by chemical synthesis or by employing recombinant technology. These methods are known in the art. Chemical synthesis, especially solid phase synthesis, is preferred for short (e.g., less than 50 residues) peptides or those containing unnatural or unusual amino acids such as D-Tyr, Ornithine, amino adipic acid, and the like. Recombinant procedures are preferred for longer polypeptides. When recombinant procedures are selected, a synthetic gene may be constructed de novo or a natural gene may be mutated by, for example, cassette mutagenesis. Set forth below are exemplary general recombinant procedures.

From a purified IGF or insulin and its amino acid sequence, for example, an IGF or insulin variant that is a peptidyl mutant of an IGF or insulin parent molecule may be produced using recombinant DNA techniques. These techniques contemplate, in simplified form, taking the gene, either natural or synthetic, encoding the peptide; inserting it into an appropriate vector; inserting the vector into an appropriate host cell; culturing the host cell to cause expression of the gene; and recovering or isolating the peptide produced thereby. Preferably, the recovered peptide is then purified to a suitable degree.

Somewhat more particularly, the DNA sequence encoding a peptidyl IGF or insulin variant is cloned and manipulated so that it may be expressed in a convenient host. DNA encoding parent polypeptides can be obtained from a genomic library, from cDNA derived from mRNA from cells expressing the peptide, or by synthetically constructing the DNA sequence (Sambrook et al, *Molecular Cloning: A Laboratory Manual* (2d ed.), Cold Spring Harbor Laboratory, N.Y., 1989).

The parent DNA is then inserted into an appropriate plasmid or vector which is used to transform a host cell. In general, plasmid vectors containing replication and control sequences which are derived from species compatible with the host cell are used in connection with those hosts. The vector ordinarily carries a replication site, as well as sequences which encode proteins or peptides that are capable of providing phenotypic selection in transformed cells.

For example, *E. coli* may be transformed using pBR322, a plasmid derived from an *E. coli* species (Mandel et al., *J. Mol. Biol.* 53: 154 (1970)). Plasmid pBR322 contains genes for ampicillin and tetracycline resistance, and thus provides easy means for selection. Other vectors include different features such as different promoters, which are often important in expression. For example, plasmids pKK223–3, pDR720, and pPL-lambda represent expression vectors with the tac, trp, or $P_L$ promoters that are currently available (Pharmacia Biotechnology).

A preferred vector is pB0475. This vector contains origins of replication for phage and *E. coli* that allow it to be shuttled between such hosts, thereby facilitating both mutagenesis and expression (Cunningham et al., *Science*, 243: 1330–1336 (1989); U.S. Pat. No. 5,580,723). Other preferred vectors are pR1Tγ and pR1T2T (Pharmacia Biotechnology). These vectors contain appropriate promoters followed by the Z domain of protein A, allowing genes inserted into the vectors to be expressed as fusion proteins.

Other preferred vectors can be constructed using standard techniques by combining the relevant traits of the vectors described above. Relevant traits include the promoter, the ribosome binding site, the decorsin or ornatin gene or gene fusion (the Z domain of protein A and decorsin or ornatin and its linker), the antibiotic resistance markers, and the appropriate origins of replication.

The host cell may be prokaryotic or eukaryotic. Prokaryotes are preferred for cloning and expressing DNA sequences to produce parent IGF-I polypeptide, segment-substituted peptides, residue-substituted peptides, and peptide variants. For example, *E. coli* K12 strain 294 (ATCC No. 31446) may be used as well as *E. coli* B, *E. coli* X1776 (ATCC No. 31537), and *E. coli* c600 and c600hfl, *E. coli* W3110 (F-, gamma-, prototrophic/ATCC No. 27325), bacilli such as *Bacillus subtilis,* and other enterobacteriaceae such as *Salmonella typhimurium* or *Serratia marcesans,* and various Pseudomonas species. The preferred prokaryote is *E. coli* W3110 (ATCC 27325). When expressed by prokaryotes the peptides typically contain an N-terminal methionine or a formyl methionine and are not glycosylated. In the case of fusion proteins, the N-terminal methionine or formyl methionine resides on the amino terminus of the fusion protein or the signal sequence of the fusion protein. These examples are, of course, intended to be illustrative rather than limiting.

In addition to prokaryotes, eukaryotic organisms, such as yeast cultures, or cells derived from multicellular organisms may be used. In principle, any such cell culture is workable. However, interest has been greatest in vertebrate cells, and propagation of vertebrate cells in culture (tissue culture) has become a reproducible procedure. *Tissue Culture,* Academic Press, Kruse and Patterson, editors (1973). Examples of such useful host cell lines are VERO and HeLa cells, Chinese Hamster Ovary (CHO) cell lines, W138, 293, BHK, COS-7 and MDCK cell lines.

A variation on the above procedures contemplates the use of gene fusions, wherein the gene encoding the desired peptide is associated, in the vector, with a gene encoding another protein or a fragment of another protein. This results in the desired peptide being produced by the host cell as a fusion with another protein or peptide. The "other" protein or peptide is often a protein or peptide which can be secreted by the cell, making it possible to isolate and purify the desired peptide from the culture medium and eliminating the necessity of destroying the host cells which arises when the desired peptide remains inside the cell. Alternatively, the fusion protein can be expressed intracellularly. It is useful to use fusion proteins that are highly expressed.

The use of gene fusions, though not essential, can facilitate the expression of heterologous peptides in *E. coli* as well as the subsequent purification of those gene products (Harris, in *Genetic Engineering,* Williamson, R., Ed. (Academic Press, London, Vol. 4,1983), p.127; Ljungquist et al., *Eur. J. Biochem.,* 186: 557–561 (1989) and Ljungquist et al., *Eur. J. Biochem.,* 186: 563–569 (1989)). Protein A fusions are often used because the binding of protein A, or more specifically the Z domain of protein A, to IgG provides an "affinity handle" for the purification of the fused protein. It has also been shown that many heterologous proteins are degraded when expressed directly in *E. coli,* but are stable when expressed as fusion proteins. Marston, *Biochem J.,* 240: 1 (1986).

Fusion proteins can be cleaved using chemicals, such as cyanogen bromide, which cleaves at a methionine, or hydroxylamine, which cleaves between an Asn and Gly residue. Using standard recombinant DNA methodology, the nucleotide base pairs encoding these amino acids may be inserted just prior to the 5' end of the gene encoding the desired peptide.

Alternatively, one can employ proteolytic cleavage off fusion protein (Carter, in *Protein Purification: From Molecular Mechanisms to Large-Scale Processes,* Ladisch et al., eds. (American Chemical Society Symposium Series No. 427, 1990), Ch 13, pages 181–193).

Proteases such as Factor Xa, thrombin, and subtilisin or its mutants, and a number of others have been successfully used to cleave fusion proteins. Typically, a peptide linker that is amenable to cleavage by the protease used is inserted between the "other" protein (e g., the Z domain of protein A) and the desired peptide. Using recombinant DNA methodology, the nucleotide base pairs encoding the linker are inserted between the genes or gene fragments coding for the other proteins. Proteolytic cleavage of the partially purified fusion protein containing the correct linker can then be carried out on either the native fusion protein, or the reduced or denatured fusion protein.

The peptide may or may not be properly folded when expressed as a fusion protein. Also, the specific peptide linker containing the cleavage site may or may not be accessible to the protease. These factors determine whether the fusion protein must be denatured and refolded, and if so, whether these procedures are employed before or after cleavage.

When denaturing and refolding are needed, typically the peptide is treated with a chaotrope, such a guanidine HCl, and is then treated with a redox buffer, containing, for example, reduced and oxidized dithiothreitol or glutathione at the appropriate ratios, pH, and temperature, such that the peptide is refolded to its native structure.

When peptides are not prepared using recombinant DNA technology, they are preferably prepared using solid-phase synthesis, such as that generally described by Merrifield, *J. Am. Chem. Soc.,* 85: 2149 (1963), although other equivalent chemical syntheses known in the art are employable. Solid-phase synthesis is initiated from the C-terminus of the peptide by coupling a protected a-amino acid to a suitable resin. Such a starting material can be prepared by attaching an α-amino-protected amino acid by an ester linkage to a chloromethylated resin or a hydroxymethyl resin, or by an amide bond to a BHA resin or MBHA resin. The preparation of the hydroxymethyl resin is described by Bodansky et al., *Chem. Ind.* (*London*), 38: 1597–1598 (1966). Chloromethylated resins are commercially available from BioRad Laboratories, Richmond, Calif. and from Lab. Systems, Inc. The preparation of such a resin is described by Stewart et al., "Solid Phase Peptide Synthesis" (Freeman & Co., San Francisco 1969), Chapter 1, pp. 1–6. BHA and MBHA resin supports are commercially available and are generally used only when the desired polypeptide being synthesized has an unsubstituted amide at the C-terminus.

The amino acids are coupled to the peptide chain using techniques well known in the art for the formation of peptide bonds. One method involves converting the amino acid to a derivative that will render the carboxyl group more susceptible to reaction with the free N-terminal amino group of the peptide fragment. For example, the amino acid can be converted to a mixed anhydride by reaction of a protected amino acid with ethylchloroformate, phenyl chloroformate, sec-butyl chloroformate, isobutyl chloroformate, pivaloyl chloride or Rike acid chlorides. Alternatively, the amino acid can be converted to an active ester such as a 2,4,5-trichlorophenyl ester, a pentachlorophenyl ester, a pentafluorophenyl ester, a p-nitrophenyl ester, a N-hydroxysuccinimide ester, or an ester formed from 1-hydroxybenzotriazole.

Another coupling method involves use of a suitable coupling agent such as NN'-dicyclohexylcarbodiimide or N,N'-diisopropyl-carbodiimide. Other appropriate coupling agents, apparent to those skilled in the art, are disclosed in E. Gross & J. Meienhofer, *The Peptides: Analysis, Structure, Biology*, Vol. I: Major Methods of Peptide Bond Formation (Academic Press, New York, 1979).

It should be recognized that the α-amino group of each amino acid employed in the peptide synthesis must be protected during the coupling reaction to prevent side reactions involving their active α-amino function. It should also be recognized that certain amino acids contain reactive side-chain functional groups (e.g., sulfhydryl, amino, carboxyl, and hydroxyl) and that such functional groups must also be protected with suitable protecting groups to prevent a chemical reaction from occurring at that site during both the initial and subsequent coupling steps. Suitable protecting groups, known in the art, are described in Gross and Meienhofer, *The Peptides: Analysis, Structure, Biology*, Vol.3: "Protection of Functional Groups in Peptide Synthesis" (Academic Press, New York, 1981).

In the selection of a particular side-chain protecting group to be used in synthesizing the peptides, the following general rules are followed. An α-amino protecting group (a) must render the α-amino function inert under the conditions employed in the coupling reaction, (b) must be readily removable after the coupling reaction under conditions that will not remove side-chain protecting groups and will not alter the structure of the peptide fragment, and (c) must eliminate the possibility of racemization upon activation immediately prior to coupling. A side-chain protecting group (a) must render the side chain functional group inert under the conditions employed in the coupling reaction, (b) must be stable under the conditions employed in removing the a-amino protecting group, and (c) must be readily removable upon completion of the desired amino acid peptide under reaction conditions that will not alter the structure of the peptide chain.

It will be apparent to those skilled in the art that the protecting groups known to be useful for peptide synthesis will vary in reactivity with the agents employed for their removal. For example, certain protecting groups such as triphenylmethyl and 2(p-biphenylyl)isopropyloxycarbonyl are very labile and can be cleaved under mild acid conditions. Other protecting groups, such as t-butyloxycarbonyl (BOC), t-amyloxycarbonyl. adamantyl-oxycarbonyl, and p-methoxybenzyloxycarbonyl are less labile and require moderately strong acids, such as trifluoroacetic, hydrochloric, or boron trifluoride in acetic acid, for their removal. Still other protecting groups, such as benzyloxycarbonyl (CBZ or Z), halobenzyloxycarbonyl, p-nitrobenzyloxycarbonyl cycloalkyloxycarbonyl, and isopropyloxycarbonyl, are even less labile and require stronger acids, such as hydrogen fluoride, hydrogen bromide, or boron trifluoroacetate in trifluoroacetic acid, for their removal. Among the classes of useful amino acid protecting groups are included:

(1) for an α-amino group, (a) aromatic urethane-type protecting groups, such as fluorenylmethyloxycarbonyl (FMOC) CBZ, and substituted CBZ, such as, eg., p-chlorobenzyloxycarbonyl, p-6-nitrobenzyloxycarbonyl, p-bromobenzyloxycarbonyl, and p-methoxybenzyloxycarbonyl, o-chlorobenzyloxycarbonyl, 2,4-dichlorobenzyloxycarbonyl, 2,6-dichlorobenzyloxycarbonyl, and the like; (b) aliphatic urethane-type protecting groups, such as BOC, t-amyloxycarbonyl, isopropyloxycarbonyl, 2-(p-biphenylyl)-isopropyloxycarbonyl, allyloxycarbonyl and the like; (c) cycloalkyl urethane-type protecting groups, such as cyclopentyloxycarbonyl, adamantyloxycarbonyl, and cyclohexyloxycarbonyl; and d) allyloxycarbonyl. The preferred α-amino protecting groups are BOC or FMOC.

(2) for the side chain amino group present in Lys, protection may be by-any of the groups mentioned above in (1) such as BOC, p-chlorobenzyloxycarbonyl, etc.

(3) for the guanidino group of Arg, protection may be by nitro, tosyl, CBZ, adamantyloxycarbonyl, 2,2,5,7,8-pentamethylchroman-6-sulfonyl or 2,3,6-trimethyl-4-methoxyphenylsulfonyl, or BOC.

(4) for the hydroxyl group of Ser, Thr, or Tyr, protection may be, for example, by C1–C4 alkyl, such as t-butyl; benzyl (BZL); substituted BZL, such as p-methoxybenzyl, p-nitrobenzyl, p-chlorobenzyl, o-chlorobenzyl, and 2,6-dichlorobenzyl.

(5) for the carboxyl group of Asp or Glu, protection may be, for example, by esterification using groups such as BZL, t-butyl, cyclohexyl, cyclopentyl, and the like.

(6) for the imidazole nitrogen of His, the tosyl moiety is suitably employed.

(7) for the phenolic hydroxyl group of Tyr, a protecting group such as tetrahydropyranyl, tert-butyl, trityl, BZL, chlorobenzyl, 4-bromobenzyl, or 2,6-dichlorobenzyl is suitably employed. The preferred protecting group is 2,6-dichlorobenzyl.

(8) for the side chain amino group of Asa or Gln, xanthyl (Xan) is preferably employed.

(9) for Met, the amino acid is preferably left unprotected.

(10) for the thio group of Cys, p-methoxybenzyl is typically employed.

The C-terminal amino acid, e.g., Lys, is protected at the N-amino position by an appropriately selected protecting group, in the case of Lys, BOC. The BOC-Lys-OH can be first coupled to the benzyhydrylamine or chloromethylated resin according to the procedure set forth in Horiki et al., *Chemistry Letters*, 165–168 (1978) or using isopropylcarbodiimide at about 25° C. for 2 hours with stirring. Following the coupling of the BOC-protected amino acid to the resin support, the α-amino protecting group is removed, as by using trifluoroacetic acid (TFA) in methylene chloride or TFA alone. The deprotection is carried out at a temperature between about 0° C. and room temperature. Other standard cleaving reagents, such as HCl in dioxane, and conditions for removal of specific α-amino protecting groups are described in the literature.

After removal of the α-amino protecting group, the remaining α-amino and side-chain protected amino acids are coupled stepwise within the desired order. As an alternative to adding each amino acid separately in the synthesis, some may be coupled to one another prior to addition to the solid-phase synthesizer. The selection of an appropriate coupling reagent is within the skill of the art. Particularly suitable as a coupling reagent is N,N'-dicyclohexyl carbodiimide or diisopropylcarbodiimide.

Each protected amino acid or amino acid sequence is introduced into the solid-phase reactor in excess, and the coupling is suitably carried out in a medium of dimethylformamide (DMF) or $CH_2Cl_2$ or mixtures thereof. If incomplete coupling occurs, the coupling procedure is repeated before removal of the N-amino protecting group prior to the coupling of the next amino acid. The success of the coupling reaction at each stage of the synthesis may be monitored. A preferred method of monitoring the synthesis is by the ninhydrin reaction, as described by Kaiser et al., *Anal. Biochem*, 34: 595 (1970). The coupling reactions can be performed automatically using well known methods, for example, a BIOSEARCH 9500™ peptide synthesizer.

Upon completion of the desired peptide sequence, the protected peptide must be cleaved from the resin support, and all protecting groups must be removed. The cleavage reaction and removal of the protecting groups is suitably accomplished simultaneously or stepwise. When the resin support is a chloro-methylated polystyrene resin, the bond anchoring the peptide to the resin is an ester linkage formed between the free carboxyl group of the C-terminal residue and one of the many chloromethyl groups present on the resin matrix. It will be appreciated that the anchoring bond can be cleaved by reagents that are known to be capable of breaking an ester linkage and of penetrating the resin matrix.

One especially convenient method is by treatment with liquid anhydrous hydrogen fluoride. This reagent not only will cleave the peptide from the resin but also will remove all protecting groups. Hence, use of this reagent will directly afford the fully deprotected peptide. When the chloromethylated resin is used, hydrogen fluoride treatment results in the formation of the free peptide acids. When the benzhydrylamine resin is used, hydrogen fluoride treatment results directly in the free peptide amines. Reaction with hydrogen fluoride in the presence of anisole and dimethylsulfide at 0° C. for one hour will simultaneously remove the side-chain protecting groups and release the peptide from the resin When it is desired to cleave the peptide without removing protecting groups, the protected peptide-resin can undergo methanolysis to yield the protected peptide in which the C-terminal carboxyl group is methylated. The methyl ester is then hydrolyzed under mild alkaline conditions to give the free C-terminal carboxyl group. The protecting groups on the peptide chain then are removed by treatment with a strong acid, such as liquid hydrogen fluoride. A particularly useful technique for methanolysis is that of Moore et al., *Pentides, Proc. Fifth Amer. Peot. Symn.*, M. Goodman and J. Meienhofer, Eds., (John Wiley, N.Y., 1977), p. 518–521, in which the protected peptide-resin is treated with methanol and potassium cyanide in the presence of crown ether.

Another method for cleaving the protected peptide from the resin when the chloromethylated resin is employed is by ammonolysis or by treatment with hydrazine. If desired, the resulting C-terminal amide or hydrazide can be hydrolyzed to the free C-terminal carboxyl moiety, and the protecting groups can be removed conventionally.

It will also be recognized that the protecting group present on the N-terminal a-amino group may be removed preferentially either before or after the protected peptide is cleaved from the support.

Purification of the polypeptides of the invention is typically achieved using conventional procedures such as preparative HPLC (including reversed phase HPLC) or other known chromatographic techniques such as gel permeation, ion exchange, partition chromatography, affinity chromatography (including monoclonal antibody columns) or counter current distribution.

The peptides of this invention may be stabilized by polymerization. This may be accomplished by crosslinking monomer chains with polyfunctional crosslinking agents, either directly or indirectly, through multi-functional polymers. Ordinarily, two substantially identical polypeptides are crosslinked at their C- or N-termini using a bifunctional crosslinking agent The agent is used to crosslink the terminal amino and/or carboxyl groups. Generally, both terminal carboxyl groups or both terminal amino groups are crosslinked to one another, although by selection of the appropriate crosslinking agent the alpha amino of one polypeptide is crosslinked to the terminal carboxyl group of the other polypeptide. Preferably, the polypeptides are substituted at their C-termini with cysteine. Under conditions well known in the art a disulfide bond can be formed between the terminal cysteines, thereby crosslinking the polypeptide chains. For example, disulfide bridges are conveniently formed by metal-catalyzed oxidation of the free cysteines or by nucleophilic substitution of a suitably modified cysteine residue. Selection of the crosslinking agent will depend upon the identities of the reactive side chains of the amino acids present in the polypeptides. For example, disulfide crosslinking would not be preferred if cysteine was present in the polypeptide at additional sites other than the C-terminus. Also within the scope hereof are peptides crosslinked with methylene bridges.

Suitable crosslinking sites on the peptides, aside from the N-terminal amino and C-terminal carboxyl groups, include epsilon amino groups found on lysine residues, as well as amino, imino, carboxyl, sulfhydryl and hydroxyl groups located on the side chains of internal residues of the peptides or residues introduced into flanking sequences. Crosslinking through externally added crosslinking agents is suitably achieved, e.g. using any of a number of reagents familiar to those skilled in the art, for example, via carbodiimide treatment of the polypeptide. Other examples of suitable multi-functional (ordinarily bifunctional) crosslinking agents are found in the literature.

The peptides of this invention also may be conformationally stabilized by cyclization. The peptides ordinarily are cyclized by covalently bonding the—and C-terminal domains of one peptide to the corresponding domain of another peptide of this invention so as to form cyclo-oligomers containing two or more iterated peptide sequences, each internal peptide having substantially the same sequence. Further, cyclized peptides (whether cyclo-oligomers or cyclo-monomers) are crosslinked to form 1–3 cyclic structures having from 2 to 6 peptides comprised therein. The peptides preferably are not covalently bonded through a-amino and main chain carboxyl groups (head to tail), but rather are crosslinked through the side chains of residues located in the—and C-terminal domains. The linking sites thus generally will be between the side chains of the residues.

Many suitable methods per se are known for preparing mono-or poly-cyclized peptides as contemplated herein. Lys/Asp cyclization has been accomplished using Na-Boc-amino acids on solid-phase support with Fmoc/9-fluorenylmethyl (OFm) side-chain protection for Lys/Asp; the process is completed by piperidine treatment followed by cyclization.

Glu and Lys side chains also have been crosslinked in preparing cyclic or bicyclic peptides: the peptide is synthesized by solid phase chemistry on a p-methylbenzhydrylamine resin. The peptide is cleaved from the resin and deprotected. The cyclic peptide is formed using diphenylphosphorylazide in diluted methylformamide. For an alternative procedure, see Schiller et al., *Peptide Protein Res.*, 25: 171–177 (1985). See also U.S. Pat No. 4,547,489. Disulfide crosslinked or cyclized peptides are generated by conventional methods. The method of Pelton et al. (*J. Med. Chem.,* 29: 2370–2375 (1986)) is suitable, except that a greater proportion of cyclo-oligomers are produced by conducting the reaction in more concentrated solutions than the dilute reaction mixture described by Pelton et al., for the production of cyclo-monomers. The same chemistry is useful for synthesis of dimers or cyclo-oligomers or cyclo-monomers. Also useful are thiomethylene bridges. Lebl and Hruby, *Tetrahedron Letters,* 25: 2067–2068 (1984). See also Cody et al., *J. Med. Chem.,* 28: 583 (1985).

The desired cyclic or polymeric peptides are purified by gel filtration followed by reversed-phase high pressure liquid chromatography or other conventional procedures. The peptides are sterile filtered and formulated into conventional pharmacologically acceptable vehicles.

The starting materials required for the processes described herein are known in the literature or can be prepared using known methods and known starting materials.

If in the peptides being created carbon atoms bonded to four nonidentical substituents are asymmetric, then the peptides may exist as diastereoisomers, enantiomers or mixtures thereof. The syntheses described above may employ racemates, enantiomers or diastereomers as starting materials or intermediates. Diastereomeric products resulting from such syntheses may be separated by chromatographic or crystallization methods. Likewise, enantiomeric product mixtures may be separated using the same techniques or by other methods known in the art Each of the asymmetric carbon atoms, when present, may be in one of two configurations (R) or S) and both are within the scope of the present invention.

The peptides of this invention are shown to bind selectively to IGFBPs. It is known to those skilled in the art that there are many uses for IGFs or insulin molecules. Therefore, administration of the peptides of this invention for purposes of agonizing an IGF or insulin action can have the same effects or uses as administration of an exogenous IGF or insulin itself These uses of IGF and insulin include the following, which may be additional to or the same as the disorders as defined above: increasing whole body, bone, and muscle growth rate in normal and hypopituitary animals; protection of body weight and nitrogen loss during catabolic states (such as fasting, nitrogen restriction, elevated corticosteroid levels, and/or diabetes); kidney regeneration; treating peripheral and central nervous system (CNS) degenerative disorders and promoting neuroprotection or repair following CNS damage or injury; treating hypoxia; promotion of wound healing; cardiac regeneration; reversal of cancer cachexia; inhibition of angiogenesis; regeneration of the gastrointestinal tract; stimulation of mammary function; counteracting IGF-I-dependent actions of GH such as metabolic stress, age-related decreases in GH activity, and adult GH deficiency; treating maturity-onset diabetes; and/or treating a specific IGF deficiency.

Additional and specific disorders for which the peptides herein are useful include growth disorders such as GH-resistant short stature, GH-insensitivity syndrome, osteoporosis, and catabolic states; disorders where treatment requires regeneration of tissues or cells, for example, peripheral nerves and supporting cells, central nervous system cells including nerves and glia, and other cells such as oligodendrocytes, muscle, skin, and bone; heart disorders, e.g., heart ischemia, cardiac myopathy, and congestive heart disorders; hyperglycemic disorders such as insulin-dependent and non-insulin-dependent diabetes mellitus and extreme insulin resistance; and renal disorders such as renal failure. These also include stimulation of an anabolic response in elderly humans, prevention of catabolic side effects of glucocorticoids, treatment of osteoporosis, stimulation of the immune system, reduction of obesity, acceleration of wound healing, acceleration of bond fracture repair, treatment of growth retardation, treatment of renal failure or insufficiency resulting in growth retardation, treatment of physiological short stature, including growth-hormone-deficient children, treating short stature associated with chronic illness, treatment of obesity and growth retardation associated with obesity, treatment of growth retardation associated with Prader-Willi syndrome and Turner's syndrome, acceleration of the recovery and reduction in the hospitalization of burn patients, treatment of interuterine growth retardation, skeletal dysplasia, hypercortisolism, and Cushings syndrome, induction of pulsatile growth hormone release, replacement of growth hormone in stressed patients, treatment of osteochondrodysplasias, Noonans syndrome, schizophrenia, depression, peripheral neuropathy, ALS, depression, Alzheimer's disease, diseases of demyelination, multiple sclerosis, and delayed wound healing, stimulation of the immune system, treatment of physcosocia depravation, treatment of pulmonary dysfunction and ventilator dependency, attenuation of protein catabolic response after a major operation, reduction of cachexia and protein loss due to chronic illness such as cancer or AIDS, treatment of hyperinsulinemia including Type II and Type I diabetes, adjuvant treatment for ovulation induction, stimulation of thymic development and prevention of the age-related decline of thymic function, treatment of immunosuppressed patients, treatment of bone marrow transplanted patients, improvement in muscle strength, mobility, diseases of muscle function, muscular dystrophy, maintenance of skin thickness, and metabolic homeostasis, enhancement of renal function and homeostasis including acute and chronic renal failure, stimulation of osteoblasts, bone remodeling, and cartilage growth, stimulation of the immune system, and growth promotion in livestock. Various IGF-I uses are found, for example, in WO 94104569; WO 96/33216; and Bondy, *Ann Intern. Med.,* 120: 593–601 (1994).

In one example, the peptides can be administered to commercially important mammals such as swine, cattle, sheep, and the like to accelerate and increase their rate and extent of growth and the efficiency of their conversion of feed into body tissue. The peptides can be administered in vivo to adults and children to stimulate IGF or insulin action.

The peptides of this invention may be administered to the mammal by any suitable technique, including oral, parenteral (e.g., intramuscular, intraperitoneal, intravenous, or subcutaneous injection or infusion or implant), nasal, pulmonary, vaginal, rectal, sublingual, or topical routes of administration, and can be formulated in dosage forms appropriate for each route of administration. The specific route of administration will depend, e.g., on the medical history of the patient, including any perceived or anticipated side effects using the peptide, the type of peptide being administered, and the particular disorder to be corrected. Most preferably, the administration is by continuous infusion (using, e.g., slow-release devices or minipumps such as osmotic pumps or skin patches), or by injection (using, e.g., intravenous or subcutaneous means).

The peptide to be used in the therapy will be formulated and dosed in a fashion consistent with good medical practice, taking into account the clinical condition of the individual patient (especially the side effects of treatment with the peptide), the site of delivery, the method of administration, the scheduling of administration, and other factors known to practitioners. The "effective amounts" of the peptide for purposes herein are thus determined by such considerations and must be amounts that result in bioavailability of the drugs to the mammal and the desired effect.

A preferred administration is a chronic administration of about two times per day for 4–8 weeks to reproduce the effects of IGF-I or insulin. Although injection is preferred, chronic infusion may also be employed using an infusion device for continuous subcutaneous (SC) infusions. An intravenous bag solution may also be employed. The key factor in selecting an appropriate dose for diabetes is the result obtained, as measured by decreases in blood glucose so as to approximate the normal range, or by other criteria for measuring treatment of diabetes as are deemed appropriate by the medical practitioner.

As a general proposition, the total pharmaceutically effective amount of the peptide administered parenterally per dose will be in a range that can be measured by a dose-response curve. For example, IGFs bound to IGFBPs or in the blood can be measured in body fluids of the mammal to be treated to determine the dosing. Alternatively, one can administer increasing amounts of the peptide to the patient and check the serum levels of the patient for IGF-I and IGF-II. The amount of peptide to be employed can be calculated on a molar basis based on these serum levels of IGF-I and IGF-II. See the Example below on displacement of IGF-I tracer from IGFBPs present in human serum. Specifically, one method for determining appropriate dosing of the peptide entails measuring IGF levels in a biological fluid such as a body or blood fluid. Measuring such levels can be done by any means, including RIA and ELISA. After measuring IGF levels, the fluid is contacted with the peptide using single or multiple doses. After this contacting step, the IGF levels are re-measured in the fluid. If the fluid IGF levels have fallen by an amount sufficient to produce the desired efficacy for which the molecule is to be administered, then the dose of the molecule can be adjusted to produce maximal efficacy. This method may be carried out in vitro or in vivo. Preferably, this method is carried out in vivo, ie., after the fluid is extracted from a mammal and the IGF levels measured, the peptide herein is administered to the mammal using single or multiple doses (that is, the contacting step is achieved by administration to a mammal) and then the IGF levels are re-measured from fluid extracted from the mammal.

Another method for determining dosing is to use antibodies to the peptide or another detection method for the peptide in the LIFA format. This would allow detection of endogenous or exogenous IGFs bound to IGFBP and the amount of peptide bound to the IGFBP.

Another method for determining dosing would be to measure the level of "free" or active IGF in blood. For some uses the level of "free" IGF would be a suitable marker of efficacy and effective doses or dosing.

For example, one method is described for detecting endogenous or exogenous IGF or insulin bound to an IGF binding protein or the amount of the peptide herein or detecting the level of unbound IGF or unbound insulin in a biological fluid. This method comprises:

(a) contacting the fluid with 1) a means for detecting the peptide that is specific for the peptide (such as a first antibody specific for epitopes on the peptide) attached to a solid-phase carrier, such that in the presence of the peptide the IGF binding sites remain available on the peptide for binding to the IGF binding protein, thereby forming a complex between the means and the IGF binding protein; and 2) the peptide for a period of time sufficient to saturate all available IGF binding sites on the IGF binding protein, thereby forming a saturated complex;

(b) contacting the saturated complex with a detectably labeled second means which is specific for the IGF binding protein (such as a second antibody specific for epitopes on the IGFBP) which are available for binding when the peptide is bound to the IGF binding protein; and (c) quantitatively analyzing the amount of the labeled means bound as a measure of the IGFBP in the biological fluid, and therefore as a measure of the amount of bound peptide and IGF binding protein, bound IGF or bound insulin and IGF binding protein, or active IGF or active insulin present in the fluid.

Given the above methods for determining dosages, in general, the amount of peptide that may be employed can be estimated, i.e., from about 10 $\mu$g/kg/day to 200 $\mu$g/kg/day might be used, based on kg of patient body weight, although, as noted above, this will be subject to a great deal of therapeutic discretion.

A further method is provided to estimate the distribution of IGFs on specific IGFBPs, e.g., on IGFBP-1 or IGFBP-3 using the LIFA format.

The peptide is suitably administered by a sustained-release system. Suitable examples of sustained-release compositions include semi-permeable polymer matrices in the form of shaped articles, e.g. films, or microcapsules. Sustained-release matrices include polylactides (U.S. Pat. No. 3,773,919, EP 58,481), copolymers of L-glutamic acid and gamma-ethyl-L-glutamate (Sidman et al., *Biopolymers*, 22, 547–556 (1983), poly(2-hydroxyethyl methacrylate) (Langer et al. *J. Biomed. Mater. Res.*, 15: 167–277 (1981), and Langer, *Chem. Tech.*, 12: 98–105(1982), ethylene vinyl acetate (Langer et al., supra) or poly-D-(-)-3-hydroxybutyric acid (EP 133,988). Sustained-release compositions also include a liposomally entrapped peptide. Liposomes containing the peptide are prepared by methods known per se: DE 3,218,121; Epstein et al., *Proc. Natl. Acad. Sci. U.S.A.* 82: 3688–3692 (1985); Hwang et al., *Proc. Natl. Acad. Sci. U.S.A.* 77: 4030–4034 (1980); EP 52,322; EP 36,676; EP 88,046; EP 143,949; EP 142,641; Japanese Pat. Appln. 83–118008; U.S. Pat. Nos. 4,485,045 and 4,544,545; and EP 102,324. Ordinarily, the liposomes are of the small (from or about 200 to 800 Angstroms) unilamellar type in which the lipid content is greater than about 30 mol. percent cholesterol, the selected proportion being adjusted for the most efficacious therapy.

PEGylated peptides having a longer life can also be employed, based on, e.g., the conjugate technology described in WO 95132003 published Nov. 30, 1995.

For parenteral administration, in one embodiment, the peptide is formulated generally by mixing each at the desired degree of purity, in a unit dosage injectable form (solution, suspension, or emulsion), with a pharmaceutically, or parenterally, acceptable carrier, i.e., one that is non-toxic to recipients at the dosages and concentrations employed and is compatible with other ingredients of the formulation. For example, the formulation preferably does not include oxidizing agents and other peptides that are known to be deleterious to polypeptides.

Generally, the formulations are prepared by contacting the peptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient Examples of such carrier vehicles include water, saline, Ringer's solution, a buffered solution, and dextrose solution. Non-aqueous vehicles such as fixed oils and ethyl oleate are also useful herein.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; glycine; amino acids such as glutamic acid, aspartic acid, histidine, or arginine; monosaccharides, disaccharides, and other carbohydrates including cellulose or its derivatives, glucose, mannose, trehalose, or dextrins; chelating agents such as EDTA; sugar alcohols such as mannitol or sorbitol; counter-ions such as sodium; non-ionic surfactants such as polysorbates, poloxamers, or polyethylene glycol (PEG); and/or neutral salts, e.g., NaCl, KCl, $MgCl_2$, $CaCl_2$, etc.

The peptide typically formulated in such vehicles at a pH of from or about 4.5 to 8. It will be understood that use of certain of the foregoing excipients, carriers, or stabilizers will result in the formation of salts of the peptide. The final preparation may be a stable liquid or lyophilized solid.

Typical formulations of the peptides as pharmaceutical compositions are discussed below. About 0.5 to 500 mg of the peptide or mixture of peptides, as the free acid or base form or as a pharmaceutically acceptable salt, is compounded with a physiologically acceptable vehicle, carrier, excipient, binder, preservative, stabilizer, flavor, etc., as called for by accepted pharmaceutical practice. The amount of active ingredient in these compositions is such that a suitable dosage in the range indicated is obtained.

The peptide to be used for therapeutic administration must be sterile. Sterility is readily accomplished by filtration through sterile filtration membranes (e.g., 0.2 micron membranes). Therapeutic compositions generally are placed into a container having a sterile access port, for example, an intravenous solution bag or vial having a stopper pierceable by a hypodermic injection needle.

The peptide ordinarily will be stored in unit or multi-dose containers, for example, sealed ampules or vials, as an aqueous solution or as a lyophilized formulation for reconstitution. As an example of a lyophilized formulation, 10-mL vials are filled with 5 mL of sterile-filtered 1% (w/v) aqueous solution of peptide, and the resulting mixture is lyophilized. The infusion solution is prepared by reconstituting the lyophilized peptide using bacteriostatic Water-for-Injection.

Combination therapy with the peptide herein and one or more other appropriate reagents that increase total IGF or insulin in the blood or enhance the effect of the peptide is also part of this invention. These reagents generally allow the peptide herein to release the generated IGF or insulin, and include growth-promoting agents.

Growth-promoting agents for this purpose include, but are not limited to, GH secretagogues that promote the release of endogenous GH in mammals to increase concentrations of the IGF in the blood. Examples include TRH, diethylstilbestrol, theophylline, enkephalins, E series prostaglandins, peptides of the VIP-secretin-glucagon-GRF family, and other GH secretagogues such as GHRP-6, GHRP-1 as described in U.S. Pat. No. 4,411,890, and benzo-fused lactams such as those disclosed in U.S. Pat No. 5,206,235. See also, e.g., WO 96/15148 published May 23, 1996. Other growth-promoting agents include GHRPs, GHRFs, GH and their analogs. For example, GHRPs are described in WO 95/17422 and WO 95/17423 both published June 29, 1995; Bowers, *J. Pediatr. Endocrinol.*, 6: 21–31 (1993); and Schoen et al., *Annual Reports in Medicinal Chemistry,* 28: 177–186 (1993). GHRFs and their analogs are described, for example, in WO 96/37514 published Nov. 28, 1996.

Additionally, GHRH, any of the IGFBPs, long-acting GH, GH plus GHBP, insulin, or a hypoglycemic agent can be employed in conjunction with the peptide herein for this purpose. In addition, IGF-I or IGF-II or an IGF with an IGFBP such as IGF-I complexed to IGFBP-3 can also be employed with the peptide herein. For example, pharmaceutical compositions containing IGF-I and IGFBP in a carrier as described in WO 94/16723 published Aug. 4, 1994 can be used in conjunction with the peptide. The entities can be administered sequentially or simultaneously with the peptide. In addition, other means of manipulating IGF status, such as regimens of diet or exercise, are also considered to be combination treatments as part of this invention.

If insulin is also administered, it can be any formulation or type of insulin as noted above. The exact dose of such insulin to be used is subject to a great deal of therapeutic discretion, and depends upon, for example, the type of disorder, the clinical profile of the patient, the type and amount of IGF-I variant or IGF-like insulin employed, the type of insulin, etc., but generally is from about 0.5 to 500 units/day of insulin. As an example, for treatment of diabetes in humans, the dose of NPH insulin is preferably from about 5 to 50 units/injection (i.e., from about 0.2 to 2 mg) twice a day subcutaneously.

Furthermore, the formulation is suitably administered along with an effective amount of a hypoglycemic agent such as a sulfonylurea. The hypoglycemic agent is administered to the mammal by any suitable technique including parenterally, intranasally, orally, or by any other effective route. Most preferably, the administration is by the oral route. For example, MICRONASE™ tablets (glyburide) marketed by Upjohn in 1.25, 2.5, and 5 mg tablet concentrations are suitable for oral administration. The usual maintenance dose for Type II diabetics, placed on this therapy, is generally in the range of from or about 1.25 to 20 mg per day, which may be given as a single dose or divided throughout the day as deemed appropriate. *Physician's Desk Reference,* 2563–2565 (1995). Other examples of glyburide-based tablets available for prescription include GLY-NASE™ brand drug (Upjohn) and DLABETA™ brand drug (Hoechst-Roussel). GLUCOTROL™ (Pratt) is the trademark for a glipizide (1-cyclohexyl-3-(p-(2-(5-methylpyrazine carboxamide)ethyl)phenyl)sulfonyl)urea) tablet available in both 5- and 10-mg strengths and is also prescribed to Type II diabetics who require hypoglycemic therapy following dietary control or in patients who have ceased to respond to other sulfonylureas. *Physician's Desk Reference,* 1902–1903 (1995). Other hypoglycemic agents than sulfonylureas, such as the biguanides (e.g., metformin and phenformin) or thiazolidinediones (e.g., troglitozone), or other drugs affecting insulin action may also be employed. If a thiazolidinedione is employed with the peptide, it is used at the same level as currently used or at somewhat lower levels, which can be adjusted for effects seen with the peptide alone or together with the dione. The typical dose of troglitazone (REZULIN™) employed by itself is about 100–1000 mg per day, more preferably 200–800 mg/day, and this range is applicable herein. See, for example, Ghazzi et al., *Diabetes,* 46: 433–439 (1997). Other thiazolidinediones that are stronger insulin-sensitizing agents than troglitazone would be employed in lower doses. In addition, the invention contemplates using gene therapy for treating a mammal, using nucleic acid encoding the peptide, if it is a peptide. Generally, gene therapy is used to increase (or overexpress) IGF or insulin levels in the mammal. Nucleic acids which encode the peptide can be used for this purpose. Once the amino acid sequence is known, one can generate several nucleic acid molecules using the degeneracy of the genetic code, and select which to use for gene therapy.

There are two major approaches to getting the nucleic acid (optionally contained in a vector) into the patient's cells for purposes of gene therapy: in vivo and ex vivo. For in vivo delivery, the nucleic acid is injected directly into the patient, usually at the site where the peptide is required. For ex vivo treatment, the patient's cells are removed, the nucleic acid is introduced into these isolated cells and the modified cells are administered to the patient either directly or, for example, encapsulated within porous membranes which are implanted into the patient See, eg. U.S. Pat. Nos. 4,892,538 and 5,283,187.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retrovirus.

The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., *J. Biol. Chem.,* 262: 4429–4432 (1987); and Wagner et al., *Proc. Natl. Acad. Sci. USA,* 87: 3410–3414(1990). For review of the currently known gene marking and gene therapy protocols, see Anderson et al., *Science,* 256: 808–813 (1992). See also WO 93/25673 and the references cited therein.

Kits are also contemplated for this invention. A typical kit would comprise a container, preferably a vial, for the peptide formulation comprising peptide in a pharmaceutically acceptable buffer and instructions, such as a product insert or label, directing the user to utilize the pharmaceutical formulation. The kit optionally includes a container, preferably a vial, for a GH, a GHRP, a GHRH, a GH secretagogue, an IGF, an IGF complexed to an IGFBP, an IGFBP, a GH complexed with a GHBP; insulin, or a hypoglycemic agent.

In another embodiment herein, a method is provided for directing endogenous IGF or insulin either away from, or towards, a particular site in a mammal comprising administering to the mammal an effective amount of the peptide herein that is specific for an IGFBP that is either prevalent at, or absent from, the site. "Sites" for this purpose include specific tissues or organs such as the heart, or such as the brain via brain-specific IGFBPs. Prevalence at the site indicates that the IGFBP in question is located at the site and constitutes a substantial or biologically important portion of the IGFBP at the site. This indication follows from the specificity for IGFBP-1 versus IGFBP-3 of the peptides demonstrated herein.

The invention will be more fully understood by reference to the following examples. They should not, however, be construed as limiting the scope of the invention. All literature and patent citations mentioned herein are expressly incorporated by reference.

EXAMPLE 1

Alanine-Scanning Mutagenesis of IGF-I and Structural Variants Introduction

An alanine-scanning mutagenesis approach (Cunningham and Wells, supra) was used to remove that portion of each side chain of IGF-I beyond the beta carbon. The contribution of these atoms to the free energy of binding of the peptide to IGFBP-1 or to IGFBP-3 was then assessed by competitive phage ELISA. In this assay, IGFBP-1 or IGFBP-3 is used to inhibit IGF-phage mutants from binding to an IGFBP-1- or IGFBP-3-coated immunosorbent plate. From a titration series of binding protein, binding (IC5o) can be calculated. Some mutants were also assessed for direct binding in BIAcore™ assays.

In the next two sets of examples, common α-amino acids may be described by the standard one- or three-letter amino acid code when referring to intermediates and final products. By common -amino acids is meant those amino acids incorporated into proteins under mRNA direction. Standard abbreviations are listed in The Merck Index, 10th Edition, pp Misc-2-Misc-3. Unless otherwise designated the common a-amino acids have the natural or "L"-configuration at the alpha carbon atom. If the code is preceded by a "D" this signifies the opposite enantiomer of the common α-amino acid. Modified or unusual α-aminoacids such as norleucine (Nle) and ornithine (Orn) are designated as described in U.S. Patent and Trademark Office Official Gazette 1114 TMOG, May 15, 1990.

Based upon the results of experiments using the IGF mutant described below, it is predicted that molecules of the type claimed herein should increase active IGF levels in a subject being treated.

Materials and Methods

Construction of Phagemid Vector and Mutagenesis

The gene encoding mature human IGF-I was amplified from pBKIGF2B (U.S. Pat. No. 5,342,763) using PCR primers 5'-AGC TGC TTT GAT ATG CAT CTC CCG AAA CTC TGT GCG GT-3' (SEQ ID NO:4) and 5'-GAG CGA TCT GGG TCT AGA CAG ATT TAG CGG GTT TCA G-3' (SEQ ID NO:5). The resulting fragment was cut with NsiI and XbaI, and ligated into pH0753 previously digested with NsiI and XbaI. pH0753 is a derivative of phGHam-g3 (Lowman et al., *Biochemistry,* 30: 10832–10838 (1991)) in which the additional XbaI site in the alkaline phosphatase promoter (PhoA) region has been deleted using the oligonucleotide 5'-AAA AGG GTA TGT AGA GGT TGA GGT-3' (SEQ ID NO:6). The ligated vector pH0753 containing the IGF-I open reading frame was named pIGF-g3. It encodes for IGF-I harboring the double mutation G1S-A70V fused to a fragment of the gene III protein (residues 249–406) from the *E. coli* bacteriophage M13. Binding of this IGF-I variant to IGFBP-1 and -3 was found to be indistinguishable from wild-type IGF-I. Alanine mutagenesis was performed using single-stranded plasmid pIGF-g3 as template (Kunkel et al., *Methods Enzymol.*, 204: 125–139 (1991)). All residues of IGF-I with the exception of cysteines and alanines were singly replaced by alanine. The resulting constructs were verified by DNA sequencing.

Binding of IGF Mutants Displayed on Phage to IGFBP-1 and -3 (Phage ELISA)

Immunosorbent plates (Nunc, MAXISORP™, 96 wells) were coated with 100 μl/well of 1 μg/mL IGFBP-1 or IGFBP-3 in PBS buffer pH 7.2 at 4° C. overnight. The plates were then blocked with 0.5% TWEEN 20™/PBS (also used as binding buffer) for 2 hours at room temperature (proteinaceous blocking agents like bovine serum albumin were avoided to prevent potential IGF or IGFBP contamination). *E. coli* cells (XL1-Blue, Stratagene) freshly transformed with phagemid vector were grown overnight in 5 mL 2YT medium (Sambrook et al., supra) in the presence of M13-VCS helper phage (Stratagene). Phage particles were harvested and resuspended in PBS buffer as described in Lowman, H. B., "Phage Display of Peptide Libraries on Protein Scaffolds," in Cabilly, S. (ed.), *Combinatorial Peptide Library Protocols* (Humana Press Inc.: Totowa, N.J., 1998), pp. 249–264. Then phage concentrations were normalized to yield a maximal ELISA signal of 0.2–0.4 for each mutant (Lowman, in Cabilly, S. (ed.), supra). Threefold serial dilutions of soluble competitor were prepared on non-absorbent microtiter plates (Nunc, F, 96 wells) with binding buffer (0.5% TWEEN™ 20/PBS) containing phage at the previously-determined concentrations. The dilution range of competitor protein extended over six orders of magnitude, starting at 5 μM for IGFBP-1 and 500 nM for IGFBP-3. After blocking, the plates containing immobilized target were washed with 0.05% TWEEN™/PBS buffer and subsequently incubated with 80 μl/well of the premixed phage-competitor solutions for 1 hour at room temperature. After washing, bound phage was detected with 80 μl/well of a solution containing a primary rabbit anti-phage polyclonal antibody and a secondary goat anti-rabbit monoclonal antibody-horseradish peroxidase conjugate in 0.5% TWEEN 20™/PBS. o-Phenylenediamine (Sigma) and tetramethylbenzidine (Kirkegaard and Perry) were used as chromogenic substrates, resulting in product detection at 492 and 450 nm, respectively. $IC_{50}$ values were determined by fitting the binding data to a generic saturation curve (Lowman, in Cabilly, S. (ed.), supra). At least two individual clones of each IGF-I mutant were assayed. Numbers in Table I represent mean±standard deviation of individually assessed $IC_{50}$ values.

Expression and Purification of IGFBP-1and IGFBP-3

Human IGFBP-1 was expressed in CHO cells and purified from the conditioned medium as described by Mortensen et al., *Endocrinology* 138: 2073–2080(1997). Recombinant human IGFBP-3 has also been cloned and expressed in mammalian cells (Wood et al., *Mol. Endocrinology*, 2: 1176–1185 (1988)). Purification from conditioned medium essentially followed the procedure described for IGFBP-1, with use of an IGF affinity column (Martin and Baxter, *J. Biol. Chem.*, 261: 8754–8760 (1986)).

Expression and Purification of Soluble IGF-I Mutants

Plasmid pBKIGF2B (U.S. Pat No. 5,342,763) expresses human wild-type IGF-I fused to the leader peptide of lamB under the control of the $P_{pho}A$ promoter. For ease of site-directed mutagenesis the phage fl origin of replication (fl ori) was introduced into plasmid pBKIGF2B. For that purpose a 466-bp BamHI fragment containing the fl ori was excised from pH0753 (Lowman et al., supra, 1991), while plasmid pBKIGF2B was linearized with EcoRI. Vector and fragment were both treated with Klenow enzyme to fill in restriction-site overhangs prior to blunt-end ligation. Correct constructs were selected for the ability to produce single-stranded phagemid DNA in the presence of M13VCS helper phage. The resulting phagemid vector was named pBKIGF2B-fl-ori and was used as template to construct the IGF-I ala-mutants of interest (see Table II) using the procedure of Kunkel et al., *Methods Enzymol.*, 204: 125–139(1991)). Every mutagenesis step was confirmed by DNA sequencing.

Expression of IGF-I mutants was as described for the IGF-I wild-type (Joly et al., *Proc. Natl. Acad. Sci. USA*, 95: 2773–2777 (1998)), but without transient over expression of oxidoreductases. The purification procedure was based on a previous protocol (Chang and Swartz, "Single-Step Solubilization and Folding of IGF-I Aggregates from *Escherichia coli*" In Cleland, J. L. (ed.), *Protein Folding In Vivo and In Vitro* (American Chemical Society, Washington, D.C., 1993), pp. 178–188), with minor adaptations. Typically, 6 g of wet cell paste (equivalent to 2 liters low phosphate medium grown for 24 hrs) was resuspended in 150 ml of 25 mM Tris-HCl pH 7.5 containing 5 mM EDTA. Cells were lysed in a microfluidizer (Microfluidics Corp., Newton, Mass.), and refractile particles containing accumulated IGF-I aggregates were collected by centrifugation at 12,000×g. Refractile particles were washed twice with lysis buffer, twice with lysis buffer containing 1% N-lauroyl-sarcosine (Sigma) to extract membrane proteins, and twice with lysis buffer again. Washed refractile bodies were resuspended at approximately 2 mg/ml in 50 mM CAPS (3-(cyclohexylamino)-1-propanesulfonic acid; Sigma) buffer pH 10.4 containing 2 M urea, 100 mM NaCl, 20% MeOH, and 2 mM DTT. This procedure combines solubilization of refractile bodies and subsequent oxidative refolding of IGF-I mutants (Chang and Swartz, supra). After 3 hrs at room temperature the refolding solutions were filtered through microconcentrator membranes (Centricon, Amicon) with a molecular weight cut off of 50 kDa. The majority of monomeric IGF-I was recovered in the eluate, while higher molecular weight contaminants were concentrated in the retentate. At this point IGF-I fractions were >95% pure, as judged from SDS-PAGE analysis. To separate correctly disulfide-bonded IGF-I from IGF-swap (containing two non-native disulfides; Hober et al., *Biochemistry* 31: 1749–1756 (1992); Miller et al, *Biochemistry*, 32: 5203–5213(1993)), refolding solutions were acidified with 5% acetic acid and loaded on a Dynamax™ C18 semi-preparative HPLC column (Varian; 10.0 mm ID) at 4 ml/min. Buffers were $H_2O$/0.1% TFA (A) and acetonitrile/0.1% TFA (B). Separation of the disulfide isomers was achieved by applying the following gradient: 0–30% B in 20 min, 30–45% B in 60 min. The ratio of native IGF-I to IGF-swap was usually about 2:1 for each mutant, with IGF-swap eluting earlier in the gradient than native IGF-I. The molecular mass of each mutant was verified by mass spectrometry. After HPLC purification, samples were lyophilized and reconstituted at approximately 1 mg/ml in 100 mM HEPES buffer, pH 7.4.

Biosensor Kinetic Measurements

The binding affinities of the IGF variants for IGFBP-1 and IGFBP-3 were determined using a BIAcore™-2000 real time kinetic interaction analysis system (BIAcore, Inc., Piscataway, N.J.) to measure association ($k_a$) and dissociation ($k_d$) rates. Carboxymethylated dextran biosensor chips (CM5, BIAcore Inc.) were activated with EDC (N-ethyl-N'-(3-dimethylaminopropyl)-carbodiimide hydrochloride) and NHS (N-hydroxysuccinimide) according to the supplier's instructions. For immobilization, IGF mutants in 20 mM sodium acetate, pH 4.8, were injected onto the biosensor chip at a concentration of 50 µg/ml to yield approximately 450–600 RU's (resonance-response units) of covalently-coupled protein. Unreacted groups were blocked with an injection of 1 M ethanolamine. Kinetic measurements were carried out by injecting two-fold serial dilutions (starting at 1 µM) of either IGFBP-1 or IGFBP-3 in running buffer (PBS, 0.05% TWEEN™ 20, 0.1% ovalbumin, 0.1% sodium azide) at 25□C using a flow rate of 20 µl/min. Association rates ($k_a$) and dissociation rates ($k_d$) were calculated separately using a 1:1 Langmuir™ association model in the BIAcore™ evaluation software v. 3.0. The equilibrium dissociation constant ($K_D$) was calculated as $k_d/k_a$.

Results

Monovalent Phage Display of IGF-I

For a rapid and comprehensive alanine scan of the 70 amino acid residues of IGF-I it was first determined whether the protein could be monovalently displayed on the surface of phage M13 (Bass et al., *Proteins*, 8: 309–314 (1990)). Phage display technology combines the advantage of rapid single-stranded DNA mutagenesis with an easy purification of the resulting mutant protein, simply by isolation of the corresponding phage particles (e.g., Cunningham et al., 1994, supra). A vector was constructed in which mature human IGF-I was fused to the carboxy-terminal domain of the M13 gene III product. This construct includes the stII signal sequence which directs the fusion protein to the periplasmic space of *E. coli* and allows monovalent display of the protein (Bass et al., supra; Lowman et al., supra, 1991). For cloning purposes the first and the last amino acids of IGF-I were changed; the resulting mutant G1S-A70V was used as the template construct for the subsequent alanine scanning mutagenesis.

When phage particles displaying IGF-I G1S-A70V were isolated and assayed in a binding competition phage ELISA for their affinity to IGFBP's, the $IC_{50}$ determined in that experiment were 8.5 nM for IGFBP-1 and 0.5 nM for IGFBP-3 (FIG. 1). These values are in good agreement with dissociation constants determined by BIAcore™ experiments using wild-type IGF-I (Heding et al., supra). Wild-type IGF-I affinities determined by radioactive immunoassays (RIA) are ~2.8 nM for IGFBP-1 and ~0.8 nM for IGFBP-3, further supporting the $IC_{50}$ values derived from phage ELISA. Additionally, phage particles displaying IGF-I G1S-A70V were efficiently captured by 11 independent monoclonal mouse anti-IGF-I antibodies immobilized on microtiter plates. These results together suggested that the displayed IGF-variant is folded correctly and accessible on the surface of the phage particles.

Ala-scanning Mutagenesis of IGF-I Binding to IGFBP-1 and IGFBP-3

All residues of G1S-A70V IGF-I with the exception of the four native alanines and six cysteines were singly substituted by alanine, using the described GlS-A70V IGF-I gIII vector as a template. Additionally, the single mutants S1G and V70A and the double-mutation restoring wild-type IGF-I were constructed. Each of these constructs was expressed in *E. coli* and displayed on phage. $IC_{50}$ values for binding to IGFBP-1 and IGFBP-3 were determined by competitive phage ELISA as shown in FIG. 1. At least two different clones of every mutant were tested. The resulting $IC_{50}$ values are listed in Table I, and the loss or gain in $IC_{50}$ for each mutant with respect to G1S-A70V is graphed in FIGS. 2A and B.

TABLE I

Apparent Affinities ($IC_{50}$) of IGF-I Variants for IGFBP-1 and IGFBP-3 Determined by Phage Display[a]

| IGF-I mutant | IGFBP-1 $IC_{50}$ (nM) | relative $IC_{50}$ | IGFBP-3 $IC_{50}$ (nM) | relative $IC_{50}$ | relative specificity |
|---|---|---|---|---|---|
| S1A | 5.2 ± 0.9 | 0.6 | 0.91 ± 0.32 | 1.2 | 0.5 |
| P2A | 11.0 ± 3.7 | 1.3 | 0.81 ± 0.18 | 1.1 | 1.2 |
| E3A | 278 ± 86 | 33.9 | 1.05 ± 0.08 | 1.4 | 24.2 |
| T4A | 19.4 ± 6.4 | 2.4 | 0.80 ± 0.02 | 1.4 | 2.2 |
| L5A | 55.3 ± 11.6 | 6.7 | 1.53 ± 0.22 | 2.0 | 3.3 |
| G7A | >1000 | >100 | 4.58 ± 0.28 | 6.1 | >16 |
| E9A | 8.6 ± 0.6 | 1.0 | 1.32 ± 0.30 | 1.8 | 0.6 |
| L10A | 311 ± 87 | 37.9 | 3.55 ± 0.33 | 4.7 | 8.1 |
| V11A* | n.d. | — | n.d. | — | — |
| D12A | 4.3 ± 0.8 | 0.5 | 1.49 ± 0.38 | 2.0 | 0.3 |
| L14A | 36.7 ± 1.1 | 4.5 | 0.90 ± 0.04 | 1.2 | 3.7 |
| Q15A | 13.9 ± 0.9 | 1.7 | 1.26 ± 0.41 | 1.7 | 1.0 |
| F16A | 57.8 ± 20.1 | 7.0 | 1.32 ± 0.25 | 1.8 | 4.0 |
| VI7A | 42.9 ± 3.2 | 5.2 | 3.67 ± 1.02 | 4.9 | 1.1 |
| G19A | 11.0 ± 2.3 | 1.3 | 0.90 ± 0.28 | 1.2 | 1.1 |
| D20A | 8.4 ± 4.1 | 1.0 | 1.11 ± 0.06 | 1.5 | 0.7 |
| R21A | 7.1 ± 1.6 | 0.9 | 0.58 ± 0.01 | 0.8 | 1.1 |
| G22A | 15.9 ± 2.8 | 1.9 | 2.07 ± 0.11 | 2.8 | 0.7 |
| F23A | 10.9 ± 1.9 | 1.3 | 2.18 ± 0.01 | 2.9 | 0.5 |
| Y24A | 13.3 ± 2.9 | 1.6 | 2.53 ± 0.76 | 3.4 | 0.5 |
| F25A | 181 ± 46 | 22.1 | 3.69 ± 0.25 | 4.9 | 4.5 |
| N26A | 9.1 ± 1.8 | 1.1 | 0.90 ± 0.07 | 1.2 | 0.9 |
| K27A | 12.8 ± 0.1 | 1.6 | 0.66 ± 0.35 | 0.9 | 1.8 |
| P28A | 9.3 ± 1.4 | 1.1 | 1.41 ± 0.05 | 1.9 | 0.6 |
| T29A | 7.3 ± 2.4 | 0.9 | 1.23 ± 0.16 | 1.6 | 0.5 |
| G30A | 7.1 ± 1.7 | 0.9 | 0.58 ± 0.11 | 0.8 | 1.1 |
| Y31A | 6.8 ± 0.5 | 0.8 | 0.73 ± 0.10 | 1.0 | 0.9 |
| G32A | 10.9 ± 1.3 | 1.3 | 0.76 ± 0.28 | 1.0 | 1.3 |
| S33A | 9.1 ± 1.0 | 1.1 | 1.01 ± 0.24 | 1.3 | 0.8 |
| S34A | 9.5 ± 0.7 | 1.2 | 1.65 ± 0.21 | 2.2 | 0.5 |
| S35A | 11.7 ± 0.6 | 1.4 | 0.47 ± 0.01 | 0.6 | 2.3 |
| R36A* | n.d. | — | n.d. | — | — |
| R37A | 12.3 ± 0.1 | 1.5 | 0.75 ± 0.08 | 1.00 | 1.5 |
| P39A* | n.d. | — | n.d. | — | — |
| Q40A | 10.2 ± 0.9 | 1.2 | 0.56 ± 0.03 | 0.7 | 1.7 |
| T41A | 13.7 ± 3.1 | 1.7 | 0.43 ± 0.06 | 0.6 | 2.9 |
| G42A | 15.7 ± 3.4 | 1.9 | 0.53 ± 0.20 | 0.7 | 2.7 |
| I43A | 31.3 ± 4.1 | 3.8 | 1.17 ± 0.07 | 1.6 | 2.4 |
| V44A | 18.8 ± 5.4 | 2.3 | 1.03 ± 0.06 | 1.4 | 1.7 |
| D45A | 4.7 ± 0.7 | 0.6 | 0.69 ± 0.21 | 0.9 | 0.6 |
| E46A | 7.9 ± 2.1 | 1.0 | 0.94 ± 0.28 | 1.3 | 0.8 |
| F49A | >1000 | >100 | 2.72 ± 1.11 | 3.6 | >28 |
| R50A | 16.2 ± 1.8 | 2.0 | 0.64 ± 0.18 | 0.9 | 2.3 |
| S51A | 13.4 ± 0.4 | 1.6 | 0.65 ± 0.35 | 0.9 | 1.9 |
| D53A | 15.3 ± 2.8 | 1.9 | 1.05 ± 0.11 | 1.2 | 1.6 |
| L54A | 23.1 ± 12.0 | 2.8 | 1.83 ± 0.91 | 2.4 | 1.2 |
| R55A | 9.0 ± 2.3 | 1.1 | 0.66 ± 0.03 | 0.9 | 1.2 |
| R56A | 13.1 ± 1.8 | 1.6 | 1.00 ± 0.19 | 1.3 | 1.2 |
| L57A | 21.8 ± 5.6 | 2.7 | 1.78 ± 0.56 | 2.4 | 1.1 |
| E58A | 11.9 ± 1.8 | 1.5 | 1.03 ± 0.47 | 1.4 | 1.1 |

TABLE I-continued

Apparent Affinities (IC$_{50}$) of IGF-I Variants for IGFBP-1
and IGFBP-3 Determined by Phage Display[a]

| | IGFBP-1 | | IGFBP-3 | | |
|---|---|---|---|---|---|
| IGF-I mutant | IC$_{50}$ (nM) | relative IC$_{50}$ | IC$_{50}$ (nM) | relative IC$_{50}$ | relative specificity |
| M59A | 13.1 ± 1.8 | 1.6 | 0.74 ± 0.14 | 1.0 | 1.6 |
| Y60A | 6.6 ± 1.8 | 0.8 | 0.52 ± 0.01 | 0.7 | 1.2 |
| P63A | >1000 | >100 | >100 | >100 | — |
| L64A | 12.1 ± 3.3 | 1.5 | 0.93 ± 0.03 | 1.2 | 1.2 |
| K65A | 12.4 ± 0.6 | 1.5 | 0.69 ± 0.05 | 0.9 | 1.6 |
| P66A | 9.4 ± 3.2 | 1.1 | 0.57 ± 0.12 | 0.8 | 1.5 |
| K68A | 10.5 ± 2.8 | 1.3 | 0.76 ± 0.23 | 1.0 | 1.3 |
| S69A | 12.8 ± 2.3 | 1.6 | 0.71 ± 0.62 | 1.2 | 1.3 |
| V70A | 19.1 ± 0.7 | 2.3 | 0.68 ± 0.15 | 0.9 | 2.6 |
| S1G | 11.2 ± 1.1 | 1.4 | 0.99 ± 0.42 | 1.3 | 1.0 |
| IGF-I WT | 8.4 ± 0.8 | 1.0 | 1.01 ± 0.42 | 1.3 | 0.8 |
| G1S-A70V | 8.2 ± 1.6 | 1.0 | 0.75 ± 0.32 | 1.0 | 1.0 |
| Ala(1-3)-IGF | 90.4 ± 9.6 | 11.0 | 1.12 ± 0.04 | 1.5 | 7.3 |
| Des(1-2)-IGF | 5.0 ± 0.1 | 0.6 | 0.53 ± 0.03 | 0.7 | 0.9 |

[a]The variants noted with an asterisk were not successfully displayed on phage (n.d.), as judged by antibody experiments described in the text. Relative IC$_{50}$ is defined as IC$_{50\ mut}$/IC$_{50\ G1S-A70V}$. Relative specificity is defined as relative IC$_{50\ IGFBP-1}$/relative IC$_{50\ IGFBP-3}$ for each variant.

The majority of the alanine mutants yielded only minor changes in IC$_{50}$ values in the phage ELISA. Importantly, wild-type IGF-I showed the same affinities for IGFBP-1 and IGFBP-3 as G1S-A70V in which background the alanine substitutions were performed (Table I, FIGS. 2A and B). Only a few residues caused considerable (>10-fold) losses in affinity when changed to alanine: E3, G7, L10, V11, F25, R36, P39, F49, and P63 for IGFBP-1 binding; V11, R36, P39, and P63 for IGFBP-3 binding. It has been noted that ala-substitutions of glycines and prolines can lead to structural perturbations of the protein backbone (Di Cera, Chem. Rev., 98: 1563–1591 (1998)).

Only a few modest improvements in binding affinity were found by alanine replacements. S1A, D12A, and D45A showed an approximately 2-fold increase in IGFBP-1 binding, while S35A and T41A showed a similar effect for IGFBP-3. However, 2-fold changes in IC$_{50}$ values are at the limit of precision in these experiments.

IGFBP-specificity Determinants

E3A, G7A, L10A, F25A, and F49 showed a differential effect in binding IGFBP-1 versus IGFBP-3. For these five IGF-I single alanine mutants the relative IC$_{50}$ for IGFBP-1 differed by more than 4-fold from the one for IGFBP-3 (FIGS. 2A and B; Table I, relative specificity). E3A and F49A showed the biggest relative specificity factors in this group. Alanine substitution of E3 had virtually no effect on IGFBP-3 affinity (1.4 fold) while binding to IGFBP-1 is weakened 34-fold. Even more dramatic, the affinity of F49A is down more than 100-fold for IGFBP-1 but only 3.6-fold for BP-3. This result was illustrated in a direct comparison by phage ELISA. Phage particles displaying IGF-I F49A were added to IGFBP-3 coated wells in the presence of soluble IGFBP-1 (FIG. 3A) or IGFBP-3 (FIG. 3B). Compared to control phage displaying IGF-I G1S-A70V, the binding curve of F49A shifted by more than two orders of magnitude in the IGFBP-1 competition (FIG. 3A). In contrast, the binding curves were similar in the IGFBP-3 competition, and the IC$_{50}$ values differed by less than a factor of 4 (FIG. 3B). Thus, E3 and F49 are two major specificity determinants for IGFBP-1 binding in the IGF-I molecule.

Residues G7, L10, and F25 appeared to be important for binding of both IGFBP's, although showing a more pronounced loss of affinity for IGFBP- 1 than for IGFBP-3 when substituted by alanines. No significant specificity determinant for IGFBP-3 was identified, such as a mutant binding much tighter to IGFBP-1 than to IGFBP-3. However, mutations E9A, D 12A, F23A, Y24A, T29A, S34A, and D45A had slightly larger (about 2-fold) effects on IGFBP-3 than on IGFBP-1 binding.

BIAcore™ Measurements of Purified Soluble IGF Mutants

For validation of the results obtained by phage ELISA, specific alanine mutants were expressed and purified for kinetic analysis using a BIAcore™ instrument. The dissociation constant (K$_D$) of wild-type IGF-I was determined to be 13 nM for IGFBP-1 and 1.5 nM for IGFBP-3 (FIGS. 5A and 5B; Table II). The difference in affinity for the IGFBP's is due to a 10-fold faster association rate (k$_a$) of IGF-I to IGFBP-3 ($3.2 \times 10^5$ versus $3.2 \times 10^4$ M$^{-1}$s$^{-1}$). These results correspond well with the absolute IC$_{50}$ values determined by phage ELISA (FIGS. 1A and 1B; Table I). As expected, the double-mutant G1S-A70V showed kinetic parameters essentially indistinguishable from wild-type (Table II).

V11A, R36A, and P39A were tested because these variants had not been displayed correctly on phage, based upon the antibody recognition experiments (see above). R36A and P39A showed wild-type kinetics for both binding proteins, whereas V11A showed a 5-fold reduction in affinity for both IGFBP-1 and IGFBP-3.

Furthermore, it was decided to examine the soluble IGF variant T4A. This residue had been implicated in IGFBP binding in earlier publications (Bayne et al., supra, J. Biol. Chem., 263; Clemmons et al., supra, 1990), but had shown modest effects in the phage assays herein. The increase in the K$_D$ values of T4A relative to wild-type IGF-I was approximately 2–3-fold higher than the IC$_{50}$ ratios determined by phage ELISA (Table II). A bigger discrepancy between the results obtained by phage and the biosensor analysis was seen for F16A. In this case the two methods differed by a factor of 4.

It has been shown that mutations in the first α-helical region have a destabilizing effect on the IGF-protein structure (Jansson et al., supra, 1997). Without being limited to any one theory, it is believed that the g3 fusion protein on the surface of the phage might be more stable than the refolded, purified soluble protein. This is supported by the BIAcore™ results obtained for F25A and F49A, two residues located outside the structurally sensitive N-terminal helix. The respective changes in K$_D$ and IC$_{50}$ values are in excellent agreement for these two mutants (Table II). The differential effect of F49A on binding to the IGFBP's was confirmed by the BIAcore™ analysis. A 70-fold decrease in affinity was measured for IGFBP-1 binding (FIG. 5C; Table II), whereas IGFBP-3 binding was reduced only 4-fold (FIG. 5D; Table II).

TABLE II

Kinetic Parameters for the Interaction of Purified IGF-I Variants with IGFBP-1 and -3 Determined by BIAcore ™ Analysis[a]

| | $k_a$ | $k_d$ | $K_D$ | relative $K_D$ | relative $IC_{50}$ |
|---|---|---|---|---|---|
| | \multicolumn{5}{c}{Binding to IGFBP-1} | | | | |
| | ($\times 10^4$ M$^{-1}$s$^{-1}$) | ($\times 10^4$ s$^{-1}$) | (nM) | | |
| IGF-I WT | 3.2 ± 0.2 | 4.1 ± 0.2 | 13.0 ± 1.0 | 1.0 | 1.0 |
| G1S-A70V | 3.2 ± 0.2 | 4.5 ± 0.01 | 14.0 ± 0.7 | 1.1 | 1.0 |
| T4A | 1.9 ± 0.2 | 16.7 ± 1.6 | 90.0 ± 11.0 | 6.9 | 2.4 |
| V11A | 1.9 ± 0.1 | 12.3 ± 0.6 | 66.5 ± 4.5 | 5.1 | — |
| F16A | 1.9 ± 0.6 | 60.3 ± 4.5 | 321 ± 98 | 25 | 6.0 |
| F25A | 1.5 ± 0.5 | 49.0 ± 5.7 | 323 ± 107 | 25 | 22 |
| R36A | 4.0 ± 0.2 | 5.6 ± 0.2 | 13.9 ± 0.8 | 1.1 | — |
| P39A | 3.1 ± 0.2 | 4.2 ± 0.1 | 13.6 ± 0.8 | 1.0 | — |
| F49A | 1.26 ± 0.8 | 115 ± 1.5 | 913 ± 551 | 70 | >100 |
| | \multicolumn{5}{c}{Binding to IGFBP-3} | | | | |
| | ($\times 10^5$ M$^{-1}$s$^{-1}$) | ($\times 10^4$ s$^{-1}$) | (nM) | | |
| IGF-I WT | 3.2 ± 0.5 | 4.7 ± 0.8 | 1.5 ± 0.3 | 1.0 | 1.4 |
| G1S-A70V | 2.9 ± 0.8 | 6.3 ± 0.5 | 2.2 ± 0.6 | 1.5 | 1.0 |
| T4A | 1.8 ± 0.6 | 5.5 ± 0.1 | 3.1 ± 1.0 | 2.1 | 1.1 |
| V11A | 3.1 ± 0.5 | 20.9 ± 2.8 | 6.7 ± 1.3 | 4.5 | — |
| F16A | 1.1 ± 0.4 | 11.4 ± 2.7 | 10.3 ± 4.7 | 6.9 | 1.8 |
| F25A | 1.5 ± 0.5 | 11.8 ± 0.1 | 7.7 ± 0.3 | 5.1 | 4.9 |
| R36A | 4.0 ± 0.1 | 4.7 ± 0.2 | 1.2 ± 0.1 | 0.8 | — |
| P39A | 2.7 ± 0.2 | 6.0 ± 0.3 | 2.2 ± 0.2 | 1.5 | — |
| F49A | 2.7 ± 0.7 | 17.1 ± 0.9 | 6.3 ± 1.7 | 4.2 | 3.6 |

[a]The relative changes in dissociation constants ($K_{D\ mut}/K_{D\ wt}$) are compared to the relative $IC_{50}$ values ($IC_{50\ mut}/IC_{50\ G1S-A70V}$) determined by phage display (Table I).

Role of the N-terminal IGF-I Residues

Surprisingly, the IGFBP-3 interaction was generally much less affected by the alanine substitutions than was the interaction with IGFBP-1, despite the fact that IGFBP-3 binds IGF-I with approximately 10-fold higher affinity. Apart from P63A, no alanine mutant exhibited a >6-fold reduction in IGFBP-3 affinity (FIGS. 2A and B and Table I).

It had previously been shown in biosensor experiments that des(1–3)-IGF-I bind IGFBP-3 with 25-fold reduced affinity (Heding et al., supra). This maturally-occurring form of IGF-I lacks the first three N-terminal residues and shows increased mitogenic potency, presumably due to its reduction in IGFBF-binding (Bagley et sl., supra). Since none of the first three amino acid side chains seem to contribute and energy to the binding of IGFBP-3 (Table I) but meverthess des(1–3)-IGF is compromised in IGFBP-3 binding, without being limited to and one theory, it is hypothesized that backbone interactions might be involved.

This hypothesis was tested by displaying on phage a triple alanine mutant (Ala(1–3)-IGF-I), substituting the first three N-terminal amino acids. If the backbone in that region contributes to the interaction with IGFBP-3 this mutant should be able to bind. Binding to IGFBP-1, however, should be reduced due to the lack of the E3 side chain (Table I). As a control the des(1–2)-IGF-I mutant was generated, testing for any potential backbone interactions with IGFBP-1 at positions 1 and 2. As expected, Ala(1–3)-IGF-I showed a decreased IGFBP-1 affinity similar to E3A but no change in IGFBP-3 affinity (Table I; FIGS. 2A and B). For des(1–2)-IGF-I, no difference in affinity was observed for both binding proteins. Combined with the observations on des(1–3)-IGF-I (Heding et al., supra), these results suggest, without limitation to any one theory, that the peptide backbone between residue 3 and 4 of IGF-I mediates important interactions with IGFBP-3.

Discussion

The functional IGFBP-1 and IGFBP-3 binding epitopes on the surface of IGF-I have been probed by alanine-scanning mutagenesis. Both binding epitopes are illustrated in FIG. 6. Individual IGF-I side-chain interactions play a much more important role for binding to IGFBP-1 than to IGFBP-3. Two major binding patches are found for IGFBP-1 (FIG. 6A). One is situated on the upper face of the N-terminal helix (composed of G7, L10, V11, L14, F25, I43, and V44) and one the lower face (composed of E3, T4, L5, F16, V17, and L54). These two binding patches are bridged by F49 and R50. For IGFBP-3, the binding epitope is more diffuse and has shifted to include G22, F23, and Y24 (FIG. 6B). Binding of IGFBP-3 is generally much less sensitive to alanine substitutions. In fact, the biggest reduction in affinity (apart from P63A, see below) is a 6-fold decrease seen for G7A. This result is intriguing since IGFBP-3 binds with 10-fold higher affinity to IGF-I than does IGFBP-1. Most probably, without limitation to any one theory, interactions originating from the IGF-I main chain backbone are contributing to the binding of IGFBP-3. This hypothesis is further substantiated by the experiments with the Ala(1–3)-IGF mutant. While the single and triple alanine substitutions have no effect on IGFBP-3 binding, deletion of the first 3 amino acids resulted in a 25-fold decrease in affinity (Bagley et al., supra; Clemmons et al., supra, 1992; Heding et al., supra). In summary, IGF-I uses different binding modes to associate with IGFBP-1 and IGFBP-3: a few amino acid side-chain interactions are important for binding to IGFBP-1, while backbone interactions seem to play a major energetic role for binding to IGFBP-3.

A recent publication has investigated the binding epitope on IGF-I for IGFBP-1 by heteronuclear NMR spectroscopy (Jansson et al., supra, 1998). The authors found that the IGF-I residues 29, 30, 36, 37, 40, 41, 63, 65, and 66 amongst others experienced chemical shift perturbations upon complexation with IGFBP-1 at 30° C. Furthermore, Jansson and co-workers identified R36, R37, and R50 to be part of the functional binding epitope and tested those alanine mutants in BIAcore™ experiments. The largest change in affinity observed by these authors was a 3-fold decrease for R50A. However, due to the structural flexibility of IGF-I already observed in the first NMR study of the hormone (Cooke et al., supra), Jansson et al. were unable to completely assign many residues in the NMR spectrum, including F49.

In similar studies of protein-protein interfaces it was found that only a few side-chain residues contribute to the bulk of free-binding energy (Clackson and Wells, *Science*, 267: 383–386 (1995); Kelley et al., *Biochemistry*, 34:10383–10392 (1995)). The same holds true for the IGF-IGFBP-1interaction. However, here, as it was noticed for tissue factor binding to factor VIIa, the magnitude of the free energy of binding ($\Delta\Delta G$) values derived from important side chains is smaller than in the case of growth hormone (Kelley et al., supra). The residues with predominant $\Delta\Delta G$ contributions were not clustered on the IGF-I surface like in the growth hormone-receptor interface (Clackson and Wells, supra), but still formed a continuous IGFBP-1 binding epitope (FIG. 6A). In contrast, the IGFBP-3 binding epitope on IGF-I was discontinuous, and side chains contributed very modest individual binding energies.

Substitution of P63 by alanine in IGF-I results in a decreased affinity for both binding proteins that cannot be measured in the concentration range used in the competition phage ELISA's. However, residue P63 is located on the opposite side of the IGF-I molecule with respect to the main binding epitope. Furthermore, it has been noticed that alanine substitutions of glycines and prolines can lead to structural changes (Di Cera, supra). In addition, Jansson et al., 1998, supra, concluded that the C-terminal part of IGF-I is not involved in direct IGFBP-1 contacts, but rather undergoes indirect conformational changes upon complex formation. An extensive characterization of antibody binding sites on IGF-I has been carried out by Manes et al., *Endocrinology* 138: 905–915 (1997). They showed simultaneous binding of IGFBP-1 or-3 to IGF-I in complex with antibodies recognizing the C-terminal D-domain. These results further support earlier observations that the D-domain, beginning with residue P63, is not involved in binding of IGFBP-1 or -3 (Bayne et al., supra, 1988).

The major discrepancy between an $IC_{50}$ ratio obtained by phage ELISA and a BIAcore™ result was observed with residue F16. As already mentioned substitution of this residue by alanine induced structural changes in the IGF-I molecule (Jansson et al., supra, 1997). The same effect was seen with the $K_D$ in the BIAcore™ results, but the affinity decrease was less pronounced in the phage ELISA experiments (see Table II). Both BIAcore™ measurements used IGF-F 16A that had been refolded during the purification procedure (Jansson et al., supra, 1997). In phage display, however, the protein of interest is translocated naturally by the secretion machinery of *E coli*. The low protein abundance in monovalent phage display (<1 molecule per phage particle) may disfavor aggregation and misfolding. Additionally, fusing IGF-I to the truncated g3 phage protein might exert a stabilizing effect on the native structure of the peptide.

The majority of IGF-I in the circulation is found in complex with IGFBP-3 and a third protein termed acid-labile subunit(ALS) (Bach and Rechler, supra; Clemmons, *Cytokine Growth Factor Rev.*, 8: 45–62 (1997); Jones and Clemmons, supra). This ternary complex of 150-kD molecular weight is unable to traverse the vasculature walls and acts as a circulating reservoir for IGF's. By this mechanism the half-life of IGF-I is dramatically increased (Simpson et al., *Growth Horm IGF Res*, 8: 83–95 (1998)). The levels of IGFBP-3 are positively regulated by IGF-I. The role of IGFBP-1, in contrast, is less clear. This class of binding proteins is generally less abundant than IGFBP-3, and its levels are negatively regulated by insulin (Bach and Rechler, supra; Clemmons, supra, 1997; Jones and Clemmons, supra).

Based on the results herein, IGFBP-specific variants of IGF-I are obtained. Combination of several alanine mutations generates a variant that binds IGFBP-1 very weakly while retaining high-affinity binding of IGFBP-3. The design of IGFBP-1 specific variants that no longer bind to IGFBP-3, can involve phage display of IGF-I and the randomization of amino acids at specific positions (Cunningham et al., 1994, supra; Lowman and Wells, *J. Mol. Biol.*, 234: 564–578 (1993)).

Conclusion

Residues in IGF-I important for binding to IGFBP-1 and IGFBP-3 have been identified. Several residues were found that determine the binding specificity for a particular IGFBP. Recent publications (Loddick et al., supra; Lowman et al., supra 1998)) have reported animal studies where increased pools of bioavailable "free" IGF-I were generated by displacing endogenous IGF-I from binding proteins. IGFBP-specific IGF-I variants may be used diagnostically and therapeutically as described above.

EXAMPLE 2

IGF-Like Insulins

It has been reported that insulin has a weak affinity of 251+/−91 nM for IGFBP-3, as measured by BIAcore™ experiments (Heding et al., supra). Thus, compared to the high-affinity complex with IGF-I (0.23 nM), insulin binds 1000-fold weaker. Hence, insulin likely presents the correct structural scaffold needed to bind IGFBP's, and if some correct residues are introduced, binding will improve.

Cascieri et al., *Endocrinology*, supra, report an approximately 1000-fold reduction in affinity to binding protein with substitution of the N-terminal region of insulin onto IGF-I, in contrast to the alanine scanning data herein (the wild-type affinity of Ala(1–3)IGF-I for IGFBP-3 (Table I)), which suggests that other substitutions near the N-terminus of IGF-I should allow IGFBP-3 binding. This is likely due to an additional residue, $Phe^{-1}$, present at the N-terminus of the IGF/insulin hybrid, ($Phe^{-1}$, $Val^1$, $Asn^2$, $Gln^3$, $His^4$, $Ser^8$, $His^9$, $Glu^{12}$, $Tyr^{15}$, $Leu^{16}$)IGF-I (numbering is that of Cascieri et al., *Endocrinology*, supra, for IGF-I). Deletion of $Phe^1$ in proinsulin or insulin is expected to improve binding to IGFBP-3. Based on alanine-scanning results, additional improvement in binding to IGFBP-3 is obtained by making mutations (proinsulin numbering) F25Y, Y26F, and T73F, because substitutions of these side chains in IGF-I affect IGFBP-3 binding (Table I) and proinsulin (as well as insulin) differs from IGF-I at these sites (FIG. 4). Binding of insulin or proinsulin to IGFBP-1 is expected to be improved by mutations Q4E, L17F, Y26F, and T49F because substitutions of these side chains in IGF-I affect IGFBP-1 binding (Table I) and proinsulin (as well as insulin) differs from IGF-I at these sites (FIG. 4).

Slieker et al., supra, proposed that long-acting analogs of insulin could be produced by engineering insulin to bind to endogenous factors. Such complexes, by analogy with IGF-I:IGFBP complexes (see, e.g., Cascieri et al., *Endocrinology*, supra) might be cleared more slowly from the circulation than the free hormone. However, the insulin variants that they reported had only poor binding affinity for IGFBP, and reduced affinity for insulin receptor (Slieker et al., supra). By defining binding determinants for IGFBP-1 and IGFBP-3 at higher resolution than earlier studies, different proinsulin and insulin variants are engineered that retain receptor binding, but achieve significant affinity for IGFBPs.

Human pro-insulin has also been displayed on phage. Therefore, binding affinities of single-site and multiple-site mutants can be readily measured by the techniques described above.

Conversion of pro-insulin to insulin occurs by excision of the region from R31 to R65 (including the mentioned residues). The resulting amino-terminal peptide of mature insulin is called B-chain, and the carboxy-terminal peptide A-chain. The chains are held together by two inter-chain disulfides. The above numbering system refers to native-sequence human pro-insulin, the sequence of which is shown in FIG. 4 compared to the native sequence of human IGF-I. If pro-insulin mutants displayed on phage successfully bind to the IGFBP's these mutations are introduced in soluble, mature insulin.

EXAMPLE 3

Treatment of Humans with Human IGF-I

This example shows the principle of how an exogenously administered peptide that binds to one or more of the IGFBPs acts to displace endogenous IGFs and how to dose a peptide herein for use in humans.

In this study human Type H diabetics were administered recombinant human IGF-I or placebo by twice daily injection at four doses (10, 20, 40 or 80 µg/kg) for 12 weeks. Blood samples were drawn, before, every two weeks during, and after (EP) the 12 weeks of treatment. The concentrations of IGF-I, IGF-II, and IGFBP-3 were measured in all the samples, with the exception of IGF-II not being measured in the samples taken from the patients treated with 10 µg/day of IGF-I.

FIG. 43 of WO 98/45427 shows the concentrations of IGF-I in the blood of the patients. The unexpected finding was the "plateau" effect of administering 40 and 80 µg of IGF-I; the same total blood concentration of IGF-I was reached with these two doses.

FIG. 44 of WO 98/45427 shows the concentrations of IGF-II in the blood of the patients. In contrast to the rising levels of IGF-I, the levels of IGF-II fell in almost a mirror image pattern to the rise in IGF-I concentrations. As with the plateauing of the rising IGF-I concentrations, the falling IGF-II concentrations also reached a plateau.

FIG. 45 of WO 98/45427 shows the concentrations of IGFBP-3 in the blood of the patients. In contrast to the clear changes in the patterns of IGF-I and IGF-II in the blood, the concentrations of IGFBP-3 showed no statistically significant or clear pattern of change.

Inspection of FIGS. 43 and 44 of WO 98/45427 reveals that the total IGF concentrations (IGF-I plus IGF-II) showed little change with treatment This was because the rise in the concentrations of IGF-I closely matched the fall in the concentrations of IGF-II. Inspection of all three Figures shows that the dose-related changes in the concentrations of IGF-I and IGF-II in the blood of the patients were not accompanied by a reduced IGFBP-3 binding protein capacity (IGFBP-3 is the major binding protein in blood).

The obvious explanation for the fall in the concentration of IGF-II, and the plateauing of IGF-I and IGF-II concentrations, is that there is a finite amount of IGF binding protein capacity and in this experiment the doses of IGF-I used caused a dose-related displacement of IGF-II from the binding proteins.

It is a logical extension of the observations in this Example to expect that any molecule with the ability to enhance levels of active IGF would show activities similar to those shown for IGF-I in this Example. In addition, from the doses of IGF-I used and the concentrations of IGFBP and IGF-I and IGF-II demonstrated, it is simple to calculate how much of a peptide should be given to increase levels of active endogenous IGF. The molar size relative to IGF-I, the affinity of the peptide for the IGFBP, and its bioavailability would be other variables taken into account to arrive at doses that increased active IGF in a human.

The present invention has of necessity been discussed herein by reference to certain specific methods and materials. It is to be understood that the discussion of these specific methods and materials in no way constitutes any limitation on the scope of the present invention, which extends to any and all alternative materials and methods suitable for accomplishing the objectives of the present invention.

What is claimed is:

1. An IGF-I variant
   (a) wherein an amino acid residue located at a single position 63 of native-sequence human IGF-I (SEQ ID NO:1) is replaced with an alanine residue or
   (b) wherein both amino acid residues at positions 1 and 70 of native-sequence human IGF-I (SEQ ID NO:1) are replaced with a serine residue and a valine residue, respectively, and an amino acid residue located at a single position 63 of native-sequence human IGF-I (SEQ ID NO:1) is replaced with an alanine residue.

2. The variant of claim 1 that has a single position replaced.

3. The variant of claim 1 that has positions 1, 70, and 63 replaced.

* * * * *